(12) United States Patent
Vachon et al.

(10) Patent No.: US 8,586,637 B2
(45) Date of Patent: Nov. 19, 2013

(54) STABLE AND COMPATIBLE POLYMER BLENDS

(75) Inventors: David John Vachon, Spokane, WA (US); Liwei Cao, Odessa, FL (US); Gary Wnek, Cleveland, OH (US)

(73) Assignees: Dais Analytic Corporation, Odessa, FL (US); Aegis Biosciences, L.L.C., Spokane, WA (US)

( * ) Notice: Subject to any disclaimer, the term of this patent is extended or adjusted under 35 U.S.C. 154(b) by 507 days.

(21) Appl. No.: 12/664,762

(22) PCT Filed: Jun. 24, 2008

(86) PCT No.: PCT/US2008/068049
§ 371 (c)(1),
(2), (4) Date: Jun. 14, 2010

(87) PCT Pub. No.: WO2009/002984
PCT Pub. Date: Dec. 31, 2008

(65) Prior Publication Data
US 2010/0261799 A1    Oct. 14, 2010

Related U.S. Application Data

(60) Provisional application No. 60/937,195, filed on Jun. 26, 2007.

(51) Int. Cl.
*A61K 47/32* (2006.01)
*C08L 53/00* (2006.01)

(52) U.S. Cl.
USPC ........................................ 514/772.1; 525/95

(58) Field of Classification Search
None
See application file for complete search history.

(56) References Cited

U.S. PATENT DOCUMENTS

| | | | |
|---|---|---|---|
| 2,283,236 A | 5/1942 | Soday | |
| 2,475,886 A | 7/1949 | Goebel | |
| 2,533,211 A | 12/1950 | Baer | |
| 3,577,357 A | 5/1971 | Winkler | |
| 3,642,953 A | 2/1972 | O'Neill et al. | |
| 3,870,841 A | 3/1975 | Makowski et al. | |
| 4,248,821 A | 2/1981 | Van Dellen | |
| 4,421,882 A | 12/1983 | Lundberg et al. | |
| 4,481,318 A | 11/1984 | Lundberg et al. | |
| 5,239,010 A | 8/1993 | Balas et al. | |
| 5,468,574 A | 11/1995 | Ehrenberg et al. | |
| 5,516,831 A | 5/1996 | Pottick et al. | |
| 5,679,482 A | 10/1997 | Ehrenberg et al. | |
| 5,840,387 A | 11/1998 | Berlowitz-Tarrant et al. | |
| 5,849,822 A | 12/1998 | Kido et al. | |
| 5,925,621 A | 7/1999 | Zaneveld et al. | |
| 5,932,619 A | 8/1999 | Zaneveld et al. | |
| 6,028,115 A | 2/2000 | Zaneveld et al. | |
| 6,110,616 A | 8/2000 | Sheikh-Ali et al. | |
| 6,239,182 B1 | 5/2001 | Zaneveld et al. | |
| 6,306,419 B1 | 10/2001 | Vachon et al. | |
| 6,348,152 B1 | 2/2002 | Kawahara et al. | |
| 6,383,391 B1 | 5/2002 | Ehrenberg et al. | |
| 6,413,298 B1 | 7/2002 | Wnek et al. | |
| 6,437,054 B1 | 8/2002 | Chisholm et al. | |
| 6,537,538 B2 | 3/2003 | Zaneveld et al. | |
| 6,699,941 B1 | 3/2004 | Handlin et al. | |
| 6,841,601 B2 | 1/2005 | Serpico et al. | |
| 7,001,950 B2 | 2/2006 | Handlin, Jr. et al. | |
| 7,067,589 B2 | 6/2006 | Bening et al. | |
| 7,098,266 B2 | 8/2006 | Weber et al. | |
| 7,169,848 B2 | 1/2007 | Bening et al. | |
| 7,169,850 B2 | 1/2007 | Handlin, Jr. et al. | |
| 7,179,860 B2 | 2/2007 | Cao et al. | |
| 7,186,779 B2 | 3/2007 | Joly et al. | |
| 2003/0106680 A1 | 6/2003 | Serpico et al. | |
| 2003/0139494 A1 | 7/2003 | Weber et al. | |
| 2004/0142910 A1 | 7/2004 | Vachon et al. | |
| 2004/0176497 A1 | 9/2004 | Segawa et al. | |
| 2005/0154144 A1 | 7/2005 | Atwood et al. | |
| 2006/0292208 A1 | 12/2006 | Vachon | |
| 2007/0004830 A1 | 1/2007 | Flood et al. | |
| 2007/0020473 A1 | 1/2007 | Umana et al. | |
| 2007/0021569 A1 | 1/2007 | Willis et al. | |
| 2007/0026251 A1 | 2/2007 | Umana | |
| 2007/0037927 A1 | 2/2007 | Yang | |
| 2007/0055015 A1 | 3/2007 | Flood et al. | |

(Continued)

FOREIGN PATENT DOCUMENTS

| CN | 1227674 | 9/1999 |
|---|---|---|
| DE | 580 366 | 7/1993 |

(Continued)

OTHER PUBLICATIONS

Vachon, D. J.; Yager, D. R. Novel sulfonated hydrogel composite with the ability to inhibit proteases and bacterial growth. Journal of Biomedical Research, 2006, vol. 76A, Issue 1, pp. 35-43.*

(Continued)

*Primary Examiner* — Robert A Wax
*Assistant Examiner* — Jessica Worsham
(74) *Attorney, Agent, or Firm* — Mueting, Raasch & Gebhardt, P.A.

(57) ABSTRACT

The present invention pertains to products and processes relating to compatible polymer blends comprising at least one sulfonated polymer and at least one non-sulfonated polymer. The sulfonated polymers may be produced using a number of sulfonating agents including a coordination complex of sulfur trioxide. The polymeric blended materials described herein are useful in a variety of applications, including as coatings for medical devices, protective clothing and fabric, laboratory equipment, vascular stents and shunts, absorbent materials and separation membranes, three-dimensional constructs, devices, and other uses.

9 Claims, 6 Drawing Sheets

(56) References Cited

U.S. PATENT DOCUMENTS

| | | | |
|---|---|---|---|
| 2008/0316678 A1 | 12/2008 | Ehrenberg et al. | |
| 2010/0031817 A1 | 2/2010 | Ehrenberg et al. | |
| 2010/0170776 A1 | 7/2010 | Ehrenberg et al. | |

FOREIGN PATENT DOCUMENTS

| | | |
|---|---|---|
| JP | 06 041412 A | 2/1994 |
| WO | WO 97/50143 | 12/1997 |
| WO | WO 03/020735 | 3/2003 |
| WO | WO 2005/030812 | 4/2005 |
| WO | WO 2008/141179 | 11/2008 |

OTHER PUBLICATIONS

Elabd, Y. A.; Napadensky, E. Sulfonation and characterization of poly(styrene-isobutylene-styrene) triblock copolymers at high ion-exchange capacities. Polymer, 2004, 45, p. 3037-3043.*

International Search Report and Written Opinion dated Jan. 30, 2009 from related International Patent Application No. PCT/US2008/068049, 9 pgs.

International Preliminary Report on Patentability dated Jan. 14, 2010 from related International Patent Application No. PCT/US2008/068049, 4 pgs.

Gilbert, Everett, "The Reactions of Sulfur Trioxide, and of its Adducts, with Organic Compounds," *Chemical Review*, Dec. 1962; 62(6): 549-589.

Jenkins et al., "Glossary of Basic Terms in Polymer Science," *International Union of Pure Applied Chemistry*, 1996; 68(12);2287-2311.

Ring et al., "Source-Based Nomenclature for Copolymers," *International Union of Pure Applied Chemistry*, 1985;57(10):1427-1440.

Samms et al., "Thermal Stability of Proton Conducting Acid Doped Polybenzimidazole in Simulated Fuel Cell Environments," *J Electrochem Soc.*, Apr. 1996;143(4):1225-1232.

Stott, "Sulfonation and Molecular Action," *Endocrine Reviews*, Oct. 2002;23(5):703-732.

Wainright et al., "Acid-Doped Polybenzimidazoles: A New Polymer Electrolyte," *J Electrochem Soc.*, Jul. 1995;142(7):L121-L123.

Wang et al., "Real-Time Mass Spectrometric Study of the Methanol Crossover in a Direct Methanol Fuel Cell," *J Electrochem Soc.*, Apr. 1996; 143(4): 1233-1239.

Weng et al., "Electro-osmotic Drag Coefficient of Water and Methanol in Polymer Electrolytes at Elevated Temperatures," *J Electrochem Soc.*, Apr. 1996; 143(4): 1260-1263.

Zecevic et al., "Kinetics of $O_2$ Reduction on a Pt Electrode Covered with a Thin Film of Solid Polymer Electrolyte," *J Electrochem Soc.*, Sep. 1997;144(9):2973-2982.

Supplementary European Search Report and Search Opinion for EP 08 77 1840; 6 pgs., 2011.

* cited by examiner

FIGURE 1 – Doxycyline Release (PBS)

STABLE AND COMPATIBLE POLYMER BLENDS

CROSS-REFERENCE TO RELATED APPLICATIONS

This application is the §371 U.S. National Stage of International Application No. PCT/US2008/068049, filed Jun. 24, 2008, published in the English language on Dec. 31, 2008 as International Publication No. WO 2009/002984, which claims the benefit of U.S. Provisional Application No. 60/937,195, filed 26 Jun. 2007, all of which are incorporated herein by reference in their entireties.

FIELD OF THE INVENTION

The subject matter disclosed herein relates to blended materials comprising sulfonated polymers (to include, for example, macromolecules, copolymers), and other polymeric compounds. Certain aspects relate to articles of manufacture composed of the blended materials disclosed herein. In other particular aspects, the blended polymeric materials may be incorporated as components in medical devices, medical instruments, vascular stents and shunts, clothing, fabric and other garments, spun fibers, woven or knit fabrics, thread, or yarn, other consumer products, moisture transfer membranes and their corresponding applications, including heat and/or fluid transfer membranes, moisture and/or heat transfer coatings, three-dimensional constructs, devices, as well as other applications.

BACKGROUND OF THE INVENTION

In the plastics industry it has been recognized that blending of different polymers can result in a composition that has properties that are superior to those of each individual component. However, one of the limitations of blending polymeric materials is that most polymer structures are immiscible (e.g., incompatible) with other (structurally different) polymers and when combined, the individual materials form phases that result in a product that does not have superior properties relative to the individual components.

Specifically, immiscible polymer blends are not thermodynamically stable. In addition, the post-mixing processing such as molding or annealing, can affect the blend morphology and reduce or eliminate any benefits of blending. In order to overcome this, an additive is often combined with the polymeric blended materials.

In other instances, when two structures are joined together in block or graft copolymer structures, the polymers oftentimes separate into phases at a microscopic scale. When the constituents of the separate phases are covalently linked to the polymer backbone, gross separation is eliminated and it is easier to produce compatible polymers, particularly block and graft copolymers. In block polymers, this micro-phase separation can result in improved material properties.

The sulfonated polymers described herein may be sulfonated by any variety of methods, including but not limited to, the specific exemplary sulfonation methods described herein. Sulfonation generally refers to an organic chemical reaction that leads to the formation of a carbon-sulfur bond. When the reacting compound contains an aromatic ring, sulfonation at the aromatic ring by the reactive (sulfonating) compound usually occurs by replacing a hydrogen atom on the aromatic ring by a sulfonic acid residue functional group by means of an electrophilic aromatic substitution reaction. However, with particular compounds, such as phenylalkanoic acids, sulfonation may occur on the carbon adjacent to the carboxyl group, rather than on the aromatic ring. In contrast to aromatic nitration or other electrophilic aromatic substitutions, aromatic sulfonation is reversible.

Sulfonation of aromatic compounds utilizing sulfur trioxide, sulfuric acid, chlorosulfonic acid, or acetyl sulfate as the sulfonating agent have been accomplished in the past with varying degrees of success. (Gilbert, $Chem. Rev.$ 62: 549-589 (1962); German Patent No. DE 580,366). The processes can be expensive, difficult, and oftentimes results in incomplete sulfonation of the compound, especially for large molecular weight oligomers or polymers. (Gilbert, supra).

Moreover, the technique of using sulfur trioxide as the sulfonating agent results in the generation of considerable amounts of undesired side-products during the course of the sulfonation reaction and subsequent work-up due to the high reactivity of the sulfur trioxide. The sulfonation side-products are frequently difficult to remove and may contaminate the final sulfonated polymer product. (Gilbert, supra).

Thus, existing methods that describe using sulfur trioxide as a sulfonating reagent to sulfonate compounds have resulted in non-uniform, incomplete sulfonation, and a high rate of formation of undesirable side-products. Further, sulfonation reactions utilizing sulfur trioxide and other reagents have, in some cases, resulted in limited ability to create sulfonated products, particularly with respect to sulfonating large molecular polymers. Moreover, excess sulfuric acid and acetic acid that result from the use of acetyl sulfate can only be removed by way of an elaborate, and expensive, absorption or extraction cleaning processes or other means. Furthermore, the use of sulfuric acid introduces water into the reaction, which can alter the ability of the reaction components to effectively solvate the polymer target. The introduction of water into the reaction through the use of sulfuric acid also prohibits sulfonating polymers with labile, or hydrolytically unstable, functional groups or moieties.

Sulfonated block copolymers have been produced by traditional sulfonation. See, for example, U.S. Pat. No. 3,577, 357. The resulting copolymer was characterized as having the general configuration A-B-(B-A) 1-5, wherein each A is a non-elastomeric sulfonated monovinyl arene polymer block and each B is a substantially saturated elastomeric alpha-olefin polymer block, said block copolymer being sulfonated to an extent sufficient to provide at least 1% by weight of sulfur in the total polymer and up to one sulfonated constituent for each monovinyl arene unit. The sulfonated polymers could be used in their produced form, or in their acid, alkali metal salt, or ammonium salt (including complex amine) forms.

The sulfonation of unsaturated styrene-diene block copolymers has also been attempted. See, for example, U.S. Pat. No. 3,642,953. In this particular example, polystyrene-polyisoprene-polystyrene was sulfonated using chlorosulfonic acid in diethyl ether. However, the sulfonic acid functionality incorporated into the polymer promotes oxidation, and the residual alkene (C=C) sites left in the polymer backbone are prone to rapid oxidation, restricting the utility of these polymers. Thus, the membranes produced with these polymers were found to be weak and could not be stabilized to make them practical for shaping or forming.

Similarly, in other examples, sulfonation of a t-butylstyrene/isoprene random copolymer and styrene/butadiene copolymer has been performed, but the products are prone to oxidative degradation, and lack flexibility to be formed or shaped. See, for example, U.S. Pat. Nos. 3,870,841 and 6,110, 616. Finally, a blend of an aliphatic hydrocarbon oil and a functionalized, selectively hydrogenated block copolymer to which has been grafted sulfonic functional groups has been prepared. See U.S. Pat. No. 5,516,831.

There is, therefore, a need in the art for novel and effective methods for the improvement of processing, mechanical properties, and dimensional stability of sulfonated polymers, and blended materials comprising sulfonated polymers (to include, macromolecules, copolymers)

SUMMARY OF EXEMPLARY ASPECTS OF THE INVENTION

Particular aspects provide a polymeric material that is water insoluble and comprises at least one sulfonated aryl-containing copolymer and at least one thermoplastic or thermosetting non-sulfonated homopolymer or copolymer selected from the group consisting of a polyurethane, a segmented polyurethane, a poly(ether urethane), a poly(carbonate urethane), a poly(siloxy urethane), a polyurethane urea, an arylene-vinyl containing block copolymer, a polysiloxane, a polyamide, a polyurethane urea, a polyketone, a polyester, a poly(ether-ester), a polyanhydride, a polyamine, a poly(ortho ester), a polyacrylate, a polyalkylene, a polycarbonate, a poly(carbonate urethane) a fluoropolymer, a polysulfone, carbohydrate polymers, a polypeptide, a polyphosphazine, a polyether, a poly(ether sulfone), a poly(vinylalcohol), poly(ethylene-co-vinyl acetate), poly(ethylene-co-vinyl alcohol), a poly(epoxide)-polyamine curing system, and an acrylate, wherein said sulfonated aryl-containing copolymer is at least 20-80 mol % sulfonated. In certain embodiments, the sulfonated copolymer comprises at least one block copolymer comprising at least two polymer end blocks (A) and at least one polymer interior block (B) wherein each (A) block is resistant to sulfonation and each (B) block is susceptible to sulfonation. In particular aspects, the sulfonated copolymer comprises an arylene-vinyl containing copolymer prepared by at least one of free radical polymerization, a coordination catalyst-based polymerization, a metallocene-based polymerization, condensation polymerization, ring-opening polymerization, reaction (step-growth) polymerization, and anionic polymerization or cationic polymerization. In certain embodiments, the polymeric material further comprises a hydrogenated or saturated central block. In certain aspects, said (A) and (B) blocks contain no significant level of olefinic unsaturation and each (A) block has an average molecular weight of between 1,000 and 60,000 and each (B) block has an average molecular weight of between 2,000 and 300,000. In particular embodiments, each (A) block comprises one or more polymerized segments selected from the group consisting of para-substituted styrene monomers, ethylene, alpha olefins of 3 to 18 carbon atoms, 1,3-cyclodiene monomers, monomers of conjugated dienes having a vinyl content less than 35 mol percent prior to hydrogenation, acrylic esters, methacrylic esters, and mixtures thereof. In particular aspects, said para-substituted styrene monomers are selected from the group consisting of para-methylstyrene, para-ethyl-styrene, para-n-proplystyrene, para-isopropylstyrene, para-n-butylstyrene, para-sec-butylstyrene, para-iso-butylstyrene, para-t-butylstyrene, para-decylstyrene isomers, and para-dodecylstyrene isomers. In particular aspects, any (A) block comprises polymerized ethylene or hydrogenated polymers of a conjugated acyclic diene and has a melting point of greater than 50° C. In certain aspects, each (B) block comprises one or more polymerized segments selected from the group consisting of alkylene monomers, vinyl aromatic monomers, unsubstituted styrene monomers, ortho-substituted styrene monomers, meta-substituted styrene monomers, alpha-methylstyrene, 1,1-diphenylethylene, 1,2-diphenylethylene, and mixtures thereof. In particular embodiments, said alkylene monomers are selected from the group consisting of variations of isobutylene, methyl cyclohexene, methylcyclopentene, and 1-methyl, 1-ethyl ethane or higher alkyl derivatives thereof. In particular aspects, each (B) block is sulfonated to the extent of 10 to 100 mol %, based on the units of arylene vinyl monomer in said (B) blocks. In particular embodiments, the mol % of arylene vinyl monomers which are unsubstituted styrene monomers, ortho-substituted styrene monomers, meta-substituted styrene monomers, alpha-methylstyrene, 1,1-diphenylethylene and 1,2-diphenylethylene in each (B) block is between 10 mol % and 100 mol %. In certain aspects, said sulfonated copolymer comprises a triblock copolymer wherein the (B) blocks comprise arylene-vinyl polymer segments and the (A) blocks comprise diene polymer segments. In certain embodiments, said (B) blocks are susceptible to sulfonation and said (A) blocks are resistant to sulfonation.

In particular embodiments, said sulfonated copolymer comprises a random block copolymer, a triblock copolymer, or a pseudo-random block copolymer in which the end blocks comprise arylene-vinyl polymer and the central blocks comprise at least one monoalkene polymer segment. In certain aspects, said monoalkene polymer segment comprises at least four carbon atoms. In certain embodiments, said sulfonated copolymer comprises an aryl-containing condensation copolymer. In particular aspects, said condensation copolymer comprises a copolymer selected from the group consisting of polyurethane, polyamide, polyester, polysiloxane, and polycarbonate. In certain aspects, said sulfonated copolymer comprises a pseudo-random block copolymer or a random block copolymer in which the end blocks are comprised of arylene-vinyl polymer and the central block is comprised of a diene polymer comprising repeat units of at least four carbon atoms. In certain embodiments, said sulfonated copolymer comprises a random copolymer comprising an arylene-vinyl monomer and a non-arylene vinyl comonomer.

In particular aspects, said sulfonated copolymer is selected from the group consisting of polyethersulfone, polyetherketone, polystyrene methylmethacrylate, polydioxanone, polylactides, polyglycolides, lactide-glycolide copolymers, and polyesters including terephthalates. In certain embodiments, said sulfonated copolymer comprises a general configuration of A-D-B-D-A, A-B-D-B-A, $(A-D-B)_n X$, $(A-B-D)_n X$, or mixtures thereof, wherein n is an integer from about 2 to about 30, and X is coupling agent residue wherein each (A) block and each (D) block is resistant to sulfonation and each (B) block is susceptible to sulfonation. In certain aspects, said (A), (B), and (D) blocks contain no significant levels of olefinic unsaturation, and wherein each (A) block has an average molecular weight of between 1,000 and 60,000 and each (B) block has an average molecular weight of between 2,000 and 300,000. In particular embodiments, each (A) block comprises one or more polymerized segments selected from the group consisting of para-substituted styrene monomers, ethylene, alpha-olefins of 3 to 18 carbon atoms, 1,3-cyclodiene monomers, monomers of conjugated dienes having a vinyl content of less than 35 mol % prior to hydrogenation, acrylic esters, methacrylic esters, and mixtures thereof. In certain aspects, said 1,3-cyclodiene or conjugated dienes are subsequently hydrogenated. In certain embodiments, each said (B) block comprises at least one segment of vinyl aromatic monomers selected from the group consisting of polymerized unsubstituted styrene monomers, polymerized ortho-substituted styrene monomers, polymerized meta-substituted styrene monomers, polymerized alpha-methylstyrene, polymerized 1,1-diphenylethylene, polymerized 1,2- diphenylethylene and mixtures thereof. In particular embodiments, each said (D) block comprises at least one polymer having a glass transition temperature of less than 20° C. and an average molecular weight of between 1,000 and 50,000. In particular aspects, each said (D) block is selected from the group consisting of a polymerized or copolymerized conjugated diene; a polymerized acrylate monomer; a silicone polymer; polymerized isobutylene and mixtures thereof. In certain embodiments, said conjugated diene comprises isoprene or 1,3-butadiene having a vinyl content prior to hydrogenation of between 20 and 80 mol percent. In particular embodiments, said (B) blocks are sulfonated to the extent of 10 to 100 mol % based on the units of vinyl aromatic monomer present. In particular aspects, the vinyl aromatic monomers are present between 10 mol % and 100 mol % and are selected from the group consisting of unsubstituted styrene monomers, ortho-substituted styrene monomers, meta-substituted styrene monomers, alpha-methylstyrene, 1,1-diphenylethylene, and 1,2-diphenylethylene. In certain aspects, each said (A) block comprises polymers of one or more para-substituted styrene monomers selected from para-methylstyrene, para-ethylstyrene, para-n-propylstyrene, para-iso-propylstyrene, para-n-butylstyrene, para-sec-butylstyrene, para-iso-butylstyrene, para-t-butylstyrene, isomers of para-decylstyrene, and isomers of para-dodecylstyrene. In particular embodiments, said (A) block comprises para-t-butylstyrene and said (B) block comprises unsubstituted styrene. In certain embodiments, said (A) block comprises para-methylstyrene and said (B) block comprises unsubstituted styrene. In particular aspects, said (D) block comprises 1,3-butadiene prior to hydrogenation, and wherein 20 to 80 mol % of the condensed butadiene units in the block have 1,2-configuration prior to hydrogenation.

Additional aspects provide an article of manufacture made with the above summarized polymeric materials, wherein said article is selected from the group consisting of a membrane, a medical device, a pharmaceutical composition, a moisture transfer membrane, a fluid-absorbing material, a fuel cell, a capacitor, a wound dressing, a fabric, a building material, a desalination membrane or device, a membrane for heating, a membrane or device for ventilating and air conditioning (HVAC), a packing material, a surface coating, a shunt, a stent, tubing, clothing, bedding, surface coatings, fluid absorbing materials, adhesives, fluid collection or storage bags, sensors, gauges, fluid filters, and the like.

Further aspects provide a method of making the above summarized polymeric materials, wherein said method comprises the steps of combining at least one sulfonated polymer in solution with at least one non-sulfonated polymer, allowing the solution to thoroughly mix, and isolating and/or processing the polymer blend. In certain embodiments, said step of isolating and/or processing the polymer blend comprises at least one of spray drying, precipitation, solvent evaporation, extruding, electrospraying, electrospinning, and precipitating the polymer blend. In particular embodiments, the method further comprises the step of converting the polymer blend to salt form.

Yet additional aspects provide a method of making an article of manufacture comprising the above summarized polymeric materials, comprising the steps of combining at least one sulfonated polymer in solution with at least one non-sulfonated polymer, allowing the solution to thoroughly mix, isolating the polymer blend, and manipulating the polymer blend to form the article. In certain embodiments, said step of manipulating the polymer blend comprises thermal lamination, transfer molding, press molding, extruding, thermal fiber-spinning, electrospinning, electrospraying, painting, dipping, pressure spraying, and the like.

BRIEF DESCRIPTION OF THE SEVERAL VIEWS OF THE DRAWING(S)

DETAILED DESCRIPTION OF THE INVENTION

Figure 1:
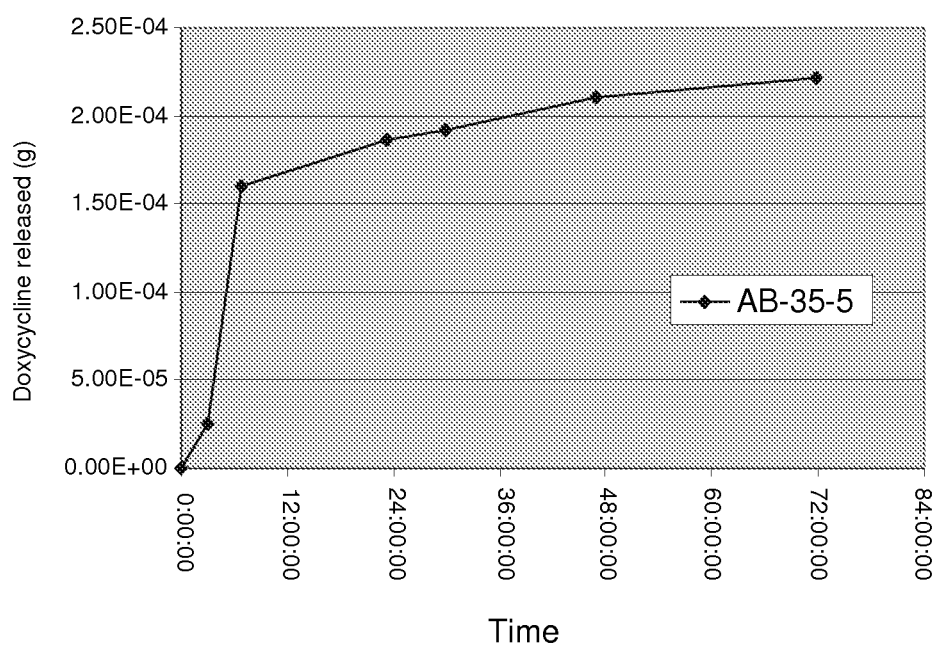
FIG. 1 shows Doxycycline release from sulfonated polymeric blended materials.

Particular aspects are directed to sulfonated polymers and sulfonated polymer blended materials, as well as methods for preparing the same. It was surprisingly found that uniform, efficacious sulfonation with sulfur trioxide was possible using the disclosed methods and polymers, which would otherwise degrade by hydrolysis (e.g., by acid, catalyzed cleavage of hydrolytically unstable bonds such as with acetylsulfate). These processes are disclosed in PCT application PCT/US2008/063243, which is hereby incorporated herein by reference in its entirety. As discussed in the PCT application, the sulfonation processes described may be utilized for sulfonating small polymers or large polymers, such as multiphase copolymers, containing alkene or arene moieties.

In certain embodiments disclosed therein, the method or process for sulfonating polymers has the ability to control the level of sulfonation and thereby control the desired properties. The methods disclosed herein entail sulfonating a polymer, such as a solid polymerized styrene, in a solvent that does not chemically react in the sulfonation process, and optionally using a coordination complex of sulfur trioxide and wherein at least one electron pair donor molecule is optionally present in the reaction solution. In certain embodiments, at least one molecule, a coordination complex of sulfur trioxide and at least one electron pair donor molecule is dissolved in one or more non-reactive solvent(s). In certain other embodiments, all of the reaction components are dissolved in one or more non-reactive solvent(s). In certain embodiments, the one or more non-reactive solvent(s) may form a coordination complex with the sulfur trioxide. In the particular embodiments wherein the non-reactive solvent forms a coordination complex with the sulfur trioxide, additional electron pair donor molecules may optionally be present in the reaction solution.

As described herein at other sections, the sulfonated polymer membranes produced by sulfonation according to the described process have demonstrated improved properties over sulfonated polymer membranes produced by other methods, including but not limited to hydrophilicity, inhibition of certain neutrophil-derived proteases, binding and release of cationic species (i.e. for ion exchange), and moisture transfer and ionic conductivity.

Since increasing hydrophilicity may result in decreasing dimensional stability or other mechanical properties, polymeric blends allow for modification so as to result in a highly improved product. For example, blending sulfonated polymeric materials with thermoplastic or thermosetting materials can improve thermal stability. Further, sulfonated polymers (in acid form) cannot generally undergo thermal processing without significant degradation due to oxidation of the polymer. While converting the polymer to the alkali salt form allows for subsequent sintering, it still has limited utility.

As described herein, we have shown in particular aspects that solution blending of the acid form of the sulfonated polymer with a non-sulfonated polymer, followed by isolation of the polymer blend by either film casting or precipitation results in a blended material that can be thermally laminated. In addition, if the non-sulfonated polymer is a material that may be extruded (such as polyurethane), then the polymeric blend can also typically be extruded.

In certain embodiments, the process of making the polymer blends includes combining at least one sulfonated polymer in solution with at least one non-sulfonated polymer, followed by isolation of the polymer blend. The blend may then be further manipulated, such as by thermal lamination, extrusion, transfer molding, injection molding, and fiber spinning (drawing). The sulfonated blend material may also be converted to salt form (for example by exposure to saline) and subsequently further manipulated, such as by melt-processing (including transfer molding, press molding, extrusion, etc.).

Polymers

As disclosed herein, specific embodiments of the sulfonation method or process that can be utilized with the polymeric blend materials comprise sulfonating polymers with sulfur trioxide however any suitable sulfonation process known in the art may be employed. The polymers that are utilized with the polymeric blends are preferably synthetic polymers but may also include other polymers such as macromolecules, as well as biological polymers including but not limited to nucleic acids (nucleotides), amino acids, peptides, polypeptides, proteins, glycoproteins, oligomers and/or polymers and/or copolymers containing either alkene and/or arene and/or hydroxyl moieties. A macromolecule, as used herein, generally refers to a molecule of high relative molecular mass, the structure of which typically comprises multiple repetition of segments derived from other molecules, such as for certain oligomers, polymers, or co-polymers. A biopolymer, as used herein, generally refers to a polymer that, at least in part, can be produced by or found in living organisms, and includes, for example, sugars (monosaccharides, disaccharides, polysaccharides, starches, and the like); amino acids; nucleotides (including oligomers); peptides; polypeptides; proteins; DNA; RNA; proteoglycans; glycoproteins, and any combination thereof. In addition, a biopolymer may comprise a combination of a naturally occurring polymer and a synthetic polymer. Some examples of combinations of biopolymers and synthetic polymers include peptidomimetics, non-natural amino acids or peptides, polypeptides and proteins containing non-natural amino acids, and others. See, for example, WO2003/020735, and Strott, *Endocrine Reviews;* 23(5):703-732; 2002.

The polymers utilized in the methods or processes of the invention may be naturally occurring, artificial, or any combination thereof. The polymers disclosed may be isolated or in a mixture or solution and/or may be chemically synthesized. The polymers may be modified (such as by reducing or dehydrogenating) prior to or subsequent to sulfonating.

As described inter alia, the polymers utilized in the processes disclosed herein may include, but are not limited to, biopolymers, oligomers and/or polymers, such as multiphase large molecular chain polymers and/or copolymers. Particular embodiments include, but are not limited to, (a) oligomers and/or polymers and/or copolymers comprising an ion-containing polymer, (b) biopolymers, or (c) block copolymers.

In certain embodiments, molecules utilized in the methods or processes of the invention comprise an ion-containing oligomeric segment or co-oligomeric segment (ionomer). Typically, ionomers utilized in the present invention relate to polyelectrolyte polymers or copolymers that contain both nonionic repeat units and at least a small amount of ion containing repeating units.

Polymers of various degrees of polymerization are also included in the present invention. As one of skill in the art would readily appreciate, the degree of polymerization generally refers to the number of repeat units or segments in an average polymer chain at a particular time in a polymerization reaction, where length is measured by monomer segments or units. Preferably, lengths include, but are not limited to, approximately 500 monomer units, 1,000 monomer units, 5,000 monomer units, 10,000 monomer units, 25,000 monomer units, 50,000 monomer units, 100,000 monomer units, 200,000 monomer units, 300,000 monomer units, 500,000 monomer units, 700,000 monomer units, or greater or any value there between.

The degree of polymerization may also be a measure of the polymer's molecular weight. Thus, the degree of polymerization is equal to the total molecular weight of the polymer divided by the total molecular weight of the repeating unit or segment. Polymers with different total molecular weights but identical composition may exhibit different physical properties. Generally, the greater the degree of polymerization correlates with the greater melting temperature and greater mechanical strength.

In certain embodiments, the oligomer and/or polymer and/or co-polymer comprise a multiphase large molecular chain molecule. In some embodiments the multiphase large molecular chain oligomers and/or polymers and/or copolymers comprise one or more arene-containing linear side chains, non-arene-containing linear side chains, saturated linear side chains, unsaturated linear side chains, or flexible hydrocarbon linear side chains.

For purposes of this invention, an "alkene moiety" refers to a hydrocarbon chain containing at least one carbon-carbon double bond. An "arene moiety" refers to a monovalent or divalent aryl or heteroaryl group. An aryl group refers to hydrocarbon ring system comprising hydrogen, 6 to 18 carbon atoms and at least one aromatic ring. For purposes of this invention, the aryl group may be a monocyclic, bicyclic, tricyclic or tetracyclic ring system, which may included fused or bridged ring systems. Aryl groups include, but are not limited to, aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pyrene, and triphenylene. Preferably, an aryl group is derived from benzene. A heteroaryl group refers to a 5- to 14-membered ring system comprising hydrogen atoms, one to thirteen carbon atoms, one to six heteroatoms selected from the group consisting of nitrogen, oxygen and sulfur, and at least one aromatic ring. For purposes of this invention, the heteroaryl group may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzindolyl, 1,3-benzodioxolyl, benzofuranyl, benzooxazolyl, benzothiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl).

For purposes of this invention, an "arene-containing linear side chain" refers to an unbranched hydrocarbon chain consisting only of hydrogen or carbon, wherein at least one carbon in the chain is replaced with an aryl or heteroaryl group, as defined above.

For purposes of this invention, a "non-arene-containing linear side chain" refers to an unbranched hydrocarbon chain consisting only of hydrogen or carbon and containing no aryl or heteroaryl groups within the chain.

For purposes of this invention, a "saturated linear side chain" refers to an unbranched hydrocarbon chain consisting only of hydrogen or carbon comprising at least one carbon-carbon double bond or at least one carbon-carbon triple bond. An "unsaturated linear side chain," as used herein, generally refers to an unbranched hydrocarbon chain consisting only of hydrogen or carbon containing no carbon-carbon double bonds and no carbon-carbon triple bonds.

For purposes of this invention, a "flexible hydrocarbon linear side chain" refers to a flexible connecting component as taught by U.S. Pat. Nos. 5,468,574 and 5,679,482, of which the disclosures of both are hereby incorporated herein by reference in their entireties.

For purposes of this invention, a "hydroxyl moiety" may refer to an oxygen atom and a hydrogen atom connected by a covalent bond.

The sulfonation process disclosed herein is particularly beneficial to sulfonating multiphase large molecules. The weight of the molecules utilized in the disclosed methods or processes are preferably at least approximately 10,000 Daltons, 15,000 Daltons, 20,000 Daltons, 25,000 Daltons, 30,000 Daltons, 40,000 Daltons, 50,000 Daltons, 60,000 Daltons, 70,000 Daltons, 80,000 Daltons, 90,000 Daltons, 1 KiloDalton, 2 KiloDaltons, 3 KiloDaltons, 4 KiloDaltons, 5 KiloDaltons, or greater or any value there between. Preferably, the size of the molecules is at least approximately 20,000 Daltons, 50,000 Daltons, 75,000 Daltons, 1 KiloDalton, 2 KiloDaltons, or any value there between.

In other embodiments, the measurement of molecular weight may be important. The average range of molecular weight (Mw) of the molecules disclosed herein includes from about 20,000 grams/mole to about 1,000,000 grams/mole, and preferably from about 50,000 grams/mole to 900,000 grams/mole.

In general, ionomers utilized in the methods or processes of the invention contain both polar and non-polar moieties. The nonpolar moieties of an ionomer are grouped together, while the polar ionic moieties tend to cluster together and separate from the nonpolar polymer backbone moieties. This ionic moiety clustering allows for thermoplasticity of the ionomers. Generally, when ionomers are heated, the ionic moieties will lose their attraction for each other and the moieties will freely move, thus allowing for thermoplastic elastomeric qualities of the ionic polymer or copolymer.

The processes disclosed herein result in polymers that can be utilized in the disclosed polymeric blends that have improved properties over the individual polymers alone. This is due, in part, to little to no crosslinking, or anhydride formation, with the sulfonated ionomeric polymers, even when the polymers contain unsaturated moieties. Without being bound by any particular theory, the sulfonation process disclosed herein may react with the unsaturated moiety, resulting in sulfonation at one or more terminal portion of the polymer.

Various types of copolymers, including block copolymers, exist that may be used with the methods or processes of the invention. For example, alternating copolymers comprise regular alternating A and B chemical or constitutional units; periodic copolymers contain A and B units arranged in a repeating sequence (e.g. (A-B-A-B-B-A-A-A-B-B)$_n$); random copolymers comprise random sequences of monomer A and B units; statistical copolymers comprise an ordering of distinct monomers within the polymer sequence that obeys statistical rules; block copolymers that are comprised of two or more homopolymer subunits linked by covalent bonds and that may be diblock, triblock, tetra-block or multi-block copolymers. (IUPAC, *Pure Appl. Chem.*, 68: 2287-2311 (1996)).

Additionally, any of the copolymers described may be linear (comprising a single main chain), or branched (comprising a single main chain with one or more polymeric side chains). Branched copolymers that have side chains that are structurally distinct from the main chain are known as graft copolymers. Individual chains of a graft copolymer may be homopolymers or copolymers, and different copolymer sequencing is sufficient to define a structural difference. For example, an A-B diblock copolymer with A-B alternating copolymer side chains is considered a graft copolymer. Other types of branched copolymers include star, brush and comb copolymers. Any one of these copolymers, or any mixture thereof, may be utilized with certain aspects of the disclosed process.

In certain embodiments disclosed herein, the molecule utilized in the methods or processes of the invention comprises a polymer comprised of at least one block. In certain embodiments, the molecule is a thermoplastic block copolymer. In other embodiments, the molecule is a block copolymer that comprises differentiable monomeric units. Preferably, at least one of the monomeric units of the block copolymer comprises an arene moiety-containing unit. In other preferred embodiments, at least one block comprises a non-arene moiety-containing unit. In certain embodiments, the block copolymer comprises at least two monomeric units arranged in statistically random order. In other embodiments, the block copolymer comprises at least two monomeric units arranged in ordered sequence. In certain embodiments, the molecule utilized in the processes disclosed herein includes not only polymers or block copolymers, but also copolymers with other ethylenically unsaturated monomers (such as acrylonitrile, butadiene, methyl methacrylate, etc.).

In certain embodiments disclosed herein, a block copolymer refers to a block copolymer having at least a first block of one or more mono alkene-arene moiety, such as styrene, ring-substituted styrene, α-substituted styrene, and any combination thereof; and a second block of a controlled distribution copolymer of a diene moiety and a mono alkene-arene moiety. The block copolymer can be any configuration of "A" and "B" blocks, and such block copolymers can be generated by methods known in the art.

For purposes of this invention, a "mono alkene-arene moiety" refers to one or more alkene moieties, as defined above, covalently bonded to an arene moiety, as defined above. An example of a "mono alkene-arene moiety" is styrene. A "poly alkene-arene moiety" refers to a two or more mono alkene-arene moieties, as defined above, covalently bonded to each other to form a chain comprising two or more mono alkene-arene moieties. An example of a "poly alkene-arene moiety" is polystyrene. A "diene moiety" refers to a hydrocarbon chain containing two carbon-carbon double bonds. In certain embodiments, the diene moiety may be conjugated, unconjugated, or cumulated.

Some specific examples of block copolymers include those described in U.S. Pat. Nos. 4,248,821; 5,239,010; 6,699,941; 7,186,779; 7,169,850; 7,169,848; 7,067,589; 7,001,950 and 6,699,941 and U.S. Patent Application Publication Nos. 20070021569; 20050154144; 20070004830; 20070020473; 20070026251; 20070037927; and 20070055015, all of which are incorporated herein by reference in their entireties.

In certain embodiments, the polymer comprises a statistical copolymer. A statistical copolymer is used herein consistent with the commonly understood usage in the art (see, for example, G. Odian, Principles of Polymerization, 1991). Statistical copolymers are derived from the simultaneous polymerization of two monomers and have a distribution of the two monomeric units along the copolymer chain, which follows Bernoullian (zero-order Markov), or first or second order Markov statistics. The polymerization may be initiated by free radical, anionic, cationic or coordinatively unsaturated (e.g., Ziegler-Natta (metallocene) catalysts), reactive polymerization, ring opening polymerization or condensation polymerization. According to Ring et al., (*Pure Appl. Chem.*, 57, 1427, 1985), statistical copolymers are the result of elementary processes leading to the formation of a statistical sequence of monomeric units that do not necessarily proceed with equal probability.

These processes can lead to various types of sequence distributions comprising those in which the arrangement of monomeric units tends toward alternation, tends toward clustering of like units, or exhibits no ordering tendency at all. Bernoullian statistics are essentially the statistics of coin tossing; copolymers formed via Bernoullian processes have the two monomers distributed randomly and are referred to as random polymers. For example, it is possible in a free radical copolymerization for the active end, in the case of one embodiment, a styryl or butadienyl radical, to have essentially no selectivity for styrene vs. butadiene. If so, the statistics will be Bernoullian, and the copolymer obtained will be random. More often than not, there will be a tendency for the propagating chain end to have some selectivity for one monomer or the other. In some cases block copolymers can be derived from the simultaneous copolymerization of two monomers when the preference of the propagating chain ends for adding the opposite monomers is very low. The resulting polymer would be categorized as a block copolymer in certain aspects of the present invention.

Statistical copolymers generally display a single glass transition temperature. Block and graft copolymers typically display multiple glass transitions, due to the presence of multiple phases. Statistical copolymers are, therefore, distinguishable from block and graft copolymers on this basis. The single glass transition temperature reflects homogeneity at the molecular level. An additional consequence of this homogeneity is that statistical copolymers, such as those of styrene and butadiene, when viewed by electron microscopy, display a single phase morphology with no microphase separation. By contrast, block and graft copolymers of styrene/butadiene, for example, are characterized by two glass transition temperatures and separation into styrene-rich domains and butadiene-rich domains. It should be noted that membranes of the invention which are produced from statistical copolymers originally having a single glass transition temperature and a single phase morphology do not necessarily exhibit a single phase morphology or a single glass transition temperature after sulfonation because of chemical changes in the polymer effected by the sulfonation, in combination with the physical changes effected by the casting processes of the invention.

Pseudo-random copolymers are a subclass of statistical copolymers which result from a weighted change in the monomer incorporation that skews the distribution from a random arrangement (i.e., Bernoullian) is defined as statistical. Linear arrangements have been described here, but branched or grafted including star arrangements of monomers are possible as well. In addition, block copolymers of styrene and hydrogenated butadiene, isoprene, or equivalent olefin can be employed. The block architecture can be monomeric units comprising diblock, triblock, graft-block, multi-arm starblock, multiblock, segmented, tapered block, or any combination thereof.

One particular advantage provided by certain embodiments includes the ability to apply the disclosed process to non-styrenic high molecular weight polymers. Thus, in certain embodiments disclosed herein, the polymers utilized in the processes disclosed do not comprise a mono alkene—arene moiety or segment, such as a styrene segment. In certain other embodiments disclosed herein, polymers utilized in the processes disclosed do not contain poly alkene—arene moieties or segments, such as polystyrene. In certain such embodiments, the polymer includes moieties or segments comprising unsaturated carbon-carbon double bonds, which are able to be sulfonated. Some examples of such polymers include, but are not limited to polybutadiene or polyisoprene. With certain polymers that are highly reactive in a particular solution, the reaction conditions may be further altered by, e.g. lowering the reaction temperature and/or further cleaning the sulfonated polymer in order to remove residual solvent and/or undesirable by-products or contaminants (?).

In particular, certain embodiments disclosed herein relate to the sulfonation of polymers comprising one or more of the following moieties: alkane, alkene, alkyne, and arene, each of which may be optionally substituted by one or more of the following functional groups: carboxylic acid, urea, ester, urethane (carbamate), alkene, amide, benzene, pyridine, indole, carbonate, thioester, arcylate/acrylic, ether, amidine, ethyl, acid versions of aliphatic compounds that contain alkenes, alkanes or alkynes, imidazole, oxazole, and other possible combinations of heteroatom containing groups susceptible to loss of water and/or disassembly. Each of the terms listed above has its standard definition known to one skilled in the art.

Some specific examples of polymers or polymer moieties or segments that may be utilized by the processes disclosed herein include but are not limited to polyethylene (PE), polypropylene (PP), polyethylene oxide (PEO), polystyrene (PS), polyesters, polycarbonate (PC), polyvinyl chloride (PVC), polyamides, halogenated polymers or copolymers such as perfluorinated copolymers, poly(methyl methacrylate) (PMMA), acrylonitrile butadiene styrene (ABS), polyamide (PA), polytetrafluoroethylene (PTFE), polylactic acid (PLA), polyvinylidene chloride (PVDC), styrene-butadiene rubber (SBR), styrene-ethylene/butylenes-styrene (SEBS); styrene-ethylene/propylene-styrene (SEPS), ethylene-styrene interpolymer (ESI), styrene acrylate, polyetherether ketone (PEEK), polyethylene terephthalate (PET or PETE), and any combination of these or others.

Solvents

The solvent(s) used in the sulfonation reaction are preferably any solvent that does not react during the sulfonation process, is easily handled in commercialization processes, and offers the appropriate solubility characteristics for the polymer undergoing sulfonation and/or the final sulfonated polymer. In certain embodiments, the solvent is preferably anhydrous.

In certain instances, the non-reacting or inert solvent comprises a hydrocarbon, preferably a halogenated hydrocarbon, such as a chlorinated hydrocarbon solvent. Some examples include, but are not limited to ethylene dichloride, perchloroethylene, trichloroethylene, 1,1,1-trichloroethane (1,1,1-TCA), dichloroethane (including 1,1-dichloroethane (1,1-DCA), and 1,2-dichloroethane (1,1-DCE)), carbon tetrachloride, vinyl chloride (VC), tetrachloroethane, chloroform (trichloromethane), dichloethane, methylene dichloride (MDC), tetrahydrofuran (THF), dimethylformamide (DMF), dimethylacetamide (DMAC), or any combination of these. In addition to chlorinated hydrocarbon solvents, other non-reacting solvent(s) include but are not limited to carbon disulfide, nitro compounds, and super-critical carbon dioxide (which behaves as a supercritical fluid, under certain conditions, and any combination of these or other non-reacting solvents.

Certain embodiments of the process disclosed herein allow for a range of the amount of solvent(s) used in the sulfonation reaction. For example, in certain embodiments, the solvent ranges from 30-99.9% of the reaction solution. In other embodiments, the solvent ranges from 50-99.5% of the reaction solution. In still other embodiments, the solvent ranges from less than approximately 10%, 8%, 5%, 4%, 3%, 2%, or 1% by weight of the polymer solution. In other particular embodiments, the solvent ranges from less than approximately 8%, 7%, 6%, 5%, 4%, 3%, 2%, or 1% by weight of the sulfur trioxide.

While the disclosed process allows for a range of molar concentrations or percent solids, one of the limiting factors is the ease of handling the reaction mixture. For example, if the solution becomes too viscous (for example, when the solids concentration is too high), homogenous dispersion of the reaction components throughout the solution may be prevented. A solution that is too viscous, presents a potential for (localized) overheating, or non-uniform heating during the reaction.

The solution viscosity of any particular sulfonated molecule (including a polymer) may be varied over a wide range and will depend on a number of variables. One of the variables is the molecular weight of the molecule, other variables include the (polymer) solids concentration used in the reaction solution, the target/final sulfonation level of the sulfonated molecule product, the solvent(s) of choice, and the temperature of the reaction mixture. By controlling the molecule solution viscosity at the outset, the very fast sulfonation kinetics can alleviate many of the aforementioned problems, such as superheating, from occurring. Thus, the proper tailoring of the reaction parameters are important for achieving a uniformly sulfonated molecule product (which provides for improved precision in polymer sulfonation). Proper tailoring of the reaction variables at the onset may allow for the application of a polymer system that allows for a range of miscibility. Additionally, the proper tuning of the reaction variables in order to maintain fast reaction kinetics can allow for production of a sulfonated molecule that is insoluble in the non-reacting solvent(s).

One advantage provided by several of the embodiments disclosed herein includes the ability to reuse or recycle the solvent(s) that are during the course of the sulfonation reaction. Because sulfonation with acetyl sulfate presents a heterogeneous reaction mixture that includes organic, mineral and organic acid, as well as aqueous components, re-capture of pure solvent following the sulfonation reaction is cumbersome and prohibitively expensive. Thus, in order to reuse the solvent(s) of the processes described herein following moderated sulfonation using the sulfur trioxide reagent as described, the solvents are captured as the sulfonated molecule product is dried, immediately following sulfonation. As the solvent(s) can be easily reused for other sulfonation reactions solvent and disposal costs can be reduced as the only waste is associated with the a small amount lost during the sulfonated molecule drying step.

For example, mixing the complete output of the sulfonation reaction (where the polymer or other molecule may or may not be in solution) with one or more non-solvent(s) of the polymer or other molecule may capture the solvent. Following precipitation of the molecule, the solvents may be collected by filtration or other methods. Generally, non-polar aliphatic hydrocarbons, which lack ionizable hydrogen atoms, are well-suited non-solvents. Some examples include, but are not limited to alkanes, such as heptane, and hexane, or cyclic alkanes, including cyclopentane, cyclohexane, cycloheptane, and cyclooctane, which are relatively non-polar. Other suitable non-solvents can be readily ascertained by one of skill in the art without undue experimentation.

The solvent(s) are then removed from the sulfonated molecule reaction mixture, such as by decanting or filtering. In certain embodiments that use non-miscible solvents that may have similar boiling points, such as dichloromethane or pentane, the solvent may be separated by fractional distillation. The sulfonated molecule is then allowed to dry, whether by ambient air, drying oven, or desiccation. The final sulfonated molecule typically produces a dry powder or flake product.

Electron Pair Donor Agent

Sulfur trioxide ($SO_3$) is a highly reactive electron acceptor or Lewis acid, and readily interacts with electron pair donors or Lewis bases to form coordination compounds, also referred to as "coordination adducts" or "coordination complexes" herein. Formation of a coordination complex with sulfur trioxide provides a method of regulating its reactivity, particularly in some of the embodiments of the sulfonation reactions described herein.

Without being bound by any particular theory, certain embodiments of the presently disclosed process benefit from the addition of an electron pair donor agent or blocking agent to the sulfonation reaction. One possible theory as to how the addition of an electron pair donor agent or blocking agent renders the sulfonation reaction more efficient is based on the attraction of the agent to the sulfur trioxide. This chemical interference may assist to regulate the sulfonation reaction as the sulfur trioxide reacts with the styrene or general aromatic ring of the polymer or other molecule. In particular aspects, the addition of an electron pair donor agent or blocking agent produced the surprising result of enhancing the sulfonation process for large molecular weight or long chain molecules utilizing sulfur trioxide in the polymeric sulfonation reaction.

Typically, the electron pair donor agent utilized in the synthetic sulfonation scheme employing sulfur trioxide in the methods of process disclosed herein includes, but is not limited to, a bidentate electron pair donor agent which is soluble in a non-reactive organic solvent. In particular embodiments, the electron pair donor agent comprises an organic species comprising at least two hetero atoms separated by at least two other atoms (for example, representing a 1,4-arrangement of heteroatoms; a 1-5-arrangement of heteroatoms, or a 1-6-arrangement of heteroatoms, etc.). Some examples of electron pair donor agents that may be used with the present process include, but are not limited to cyclic or non-cyclic carboxylic acid esters, amines (including tertiary amines), sulfides, sulfoxides, carboxylic acids, thiols, amides, ethers, thioethers, and sulfonamides. In certain embodiments, at least one electron pair donor agent comprises trimethylamine, triethylamine, pyridine, N,N'-diethylaniline, 2-methlypyridine, 2,6-dimethylpyridine, N-ethylmorpholine, 1,2-dimethoxyethane, 1,3-dimethoxypropane, 1,4-dioxane, or others.

Additives

Compatible polymer blends can often be produced or enhanced by addition of monomeric or polymeric materials without any chemical reaction. A variety of additives have been utilized in polymeric blends, including the monomeric additives of solvents, plasticizers, surfactants, fibers, and fillers; and the polymeric additives including but not limited to block copolymers or graft copolymers. Additionally, impact modifiers may be added, such as acrylics. Finally, the sulfonic acid component of the blend may be neutralized or ion exchanged to incorporate ammonia or ammonium such as $NH_4+$, benzyl trimethyl ammonium or catalytic metal ions (oxovanadium ion, cobalt ion, rhodium ion, etc.).

Reaction Conditions

A feature of the methods or processes of the invention includes the surprising result of a controllable sulfonation reaction that results in a sulfonated molecule product with low levels, or the absence of, undesirable side-products or degradation. In contrast, even when very low temperatures are utilized for sulfonation reactions using uncomplexed sulfur trioxide, sulfonation leads to a complex mixture of sulfonated polymer product and a variety of undesirable side reactions. Typically, dehydrogenation and oxidation accompany sulfonation, and the end product contains complex mixtures of hydroxyl and carbonyl compounds, carboxylic acids, and unsaturated compounds, as well as their derived sulfates, sulfonic acids, sulfones, sultones and sulfonate esters. It is expensive and cumbersome to purify the sulfonated polymer in the presence of these undesirable sulfonation reaction side-products.

Several factors contribute to the efficiency of the sulfonation processes disclosed herein, including, but not limited to, the sulfonating agent, the polymer, the molecular weight of the polymer, the solvent, the concentration of reactants in the sulfonation solution, the rate and amount of agitation or mixing, the purity of the solvent and reactants, the temperature of the reaction and reactants, the molar ratios of reactants, solvent(s) and optional electron pair donor agent(s), the modes of reactant feeding, the size of the sulfonation vessel, the sequence of addition to the solution of each of the reactants, the aging of the finished reaction mixture, and others.

In some embodiments, the concentration of the polymer utilized in the sulfonation reaction solution is less than approximately 50% solids by weight, less than approximately 40% solids, less than approximately 30% solids, less than approximately 20% solids, less than approximately 10% solids, less than approximately 5% solids, less than approximately 4% solids, less than approximately 3.5% solids, less than approximately 3% solids, less than approximately 2% solids, less than approximately 1% solids, less than approximately 0.5% solids, or less or any value there between. In some particular embodiments, the concentration of the polymer utilized in the sulfonation reaction solution is in the range of approximately 2-5% solids. In still other particular embodiments, the concentration of the polymer utilized in the sulfonation reaction solution is approximately 3.5% solids.

In certain embodiments disclosed herein, the concentration of at least one electron pair donor agent is at least approximately 1.0 mol % donor polymer per mole of sulfur trioxide. In other embodiments, the concentration of at least one electron pair donor molecule is at least approximately 2.0 mol %, 3.0 mol %, 4.0 mol %, 5.0 mol %, 6.0 mol %, 7.0 mol %, 8.0 mol %, 9.0 mol %, 10 mol %, 20 mol %, 30 mol %, 40 mol %, 50 mol %, 60 mol %, 70 mol %, 80 mol %, 90 mol %, 100 mol %, 110 mol %, 120 mol %, 150 mol %, 175 mol %, 200 mol %, 225 mol %, 250 mol %, 275 mol %, 300 mol %, 325 mol %, 350 mol %, or any value there between donor agent per mole of sulfur trioxide.

The various polymers that may be utilized in the sulfonation reaction disclosed herein may be exposed to the sulfonating reagent in the form of a solid, liquid, or gas (including vapor). The molecular species or sulfonating reagents may be completely or partially soluble in the reaction medium such that the reaction medium comprises a solution, mixture, gel, emulsion, colloidal suspension, sol, or the like or any combination thereof. In some particular embodiments, the polymer is introduced into the sulfonation reaction in a solid form, including the form of pellets, crumb, chunks, flat sheets, dispersed particles, or the like. In other embodiments, the polymer is introduced to the sulfonation reaction in liquid form (in solution or in mixture form) with the other reaction components. Still, in other particular embodiments, the molecule is introduced to the sulfonation reaction in a gaseous or vapor form. In some embodiments, the molecule is introduced into the sulfonation reaction in any combination of these forms.

The degree of sulfonation is defined in the art as the quotient of the total number of sulfonic acid groups in the molecule and the total number of self-repeating monomeric units. Adjusting one or more of the several factors that contribute to the efficiency of the sulfonation process described herein may regulate the degree of sulfonation. For example, by increasing or decreasing the temperature beyond the preferred range, the sulfonation reaction slows and the resulting sulfonated polymer exhibits a low percent by weight of sulfonic acid residues. Moreover, by increasing or decreasing the speed beyond the preferred range, the polymer may precipitate out of solution and the resulting sulfonated polymer is not uniformly sulfonated.

As described inter alia, the degree of sulfonation of a particular polymer disclosed herein may range from approximately 2-100 mole mol %. Preferably, the sulfonated polymers disclosed herein exhibit a degree of sulfonation of approximately 10 mol %, 20 mol %, 30 mol %, 40 mol %, 50 mol %, 60 mol %, 70 mol %, 80 mol %, 90 mol %, 95 mol %, 96 mol %, 97 mol %, 98 mol %, 99%, 100 mol %, or any value there between. Most preferably, the sulfonated polymers disclosed herein exhibit a degree of sulfonation of approximately 25 mol % to 80 mol %.

Certain embodiments of the disclosed process are characterized by a low reaction temperature and short reaction time. Using a low reaction temperature facilitates production of a highly efficiently sulfonated product polymer that exhibits a desirable and controllable degree of uniform sulfonation with little to no generation of undesirable side-products. In certain embodiments, the starting temperature of the reactants and/or the temperature of the reaction mixture and/or the temperature of the sulfonation reaction is approximately $-40°$ C., $-30°$ C., $-25°$ C., $-20°$ C., $-15°$ C., $-10°$ C., $-5°$ C., $0°$ C., $5°$ C., $10°$ C., $15°$ C., $20°$ C., $25°$ C., $30°$ C., or any value there between. The starting temperature or reaction temperature or sulfonation temperature may all be the same or each temperature may be different. For example, the starting temperature may be approximately $-20°$ C., and increase slightly as the reaction mixture is mixed or processed due to the increase in kinetic energy. Furthermore, the sulfonation reaction itself may be exothermic, thus increasing the reaction temperature.

The lower limit for the temperature of the reaction mixture during the reaction is chosen such that a relatively uniform solution is still present, i.e. such that no component of the mixture is present as a solid aggregate. While the reaction temperature ranges may vary somewhat, the sulfonation reaction slows at colder temperatures, while degradation of the polymer may occur and/or formation of undesirable reaction side-products (such as crosslinking) occurs at temperatures that are too high.

In addition, the sulfonation process can be carried out either under normal pressure or under increased pressure. Overall pressure is preferably in the range of approximately 1-200 bar. In certain embodiments, the pressure is approximately 1 bar, 5 bar, 10 bar, 20 bar, 50 bar, 75 bar, 100 bar, 120 bar, 150 bar, 180 bar, 200 bar, or any value there between.

Another surprising result of the presently disclosed process relates to using the thermo-kinetic effect of the high speed mixer wherein the shear rate is from approximately $5\ s^{-1}$, $10\ s^{-1}$, $15\ s^{-1}$, $20\ s^{-1}$, $30\ s^{-1}$, $40\ s^{-1}$, $50\ s^{-1}$, or greater or any value there between that is capable of increasing the temperature of the sulfonation reaction in a controlled and uniform manner. It was found that when the temperature of the sulfonation reaction was uniformly increased, the reaction yields a more uniformly sulfonated polymer. Moreover, when the sulfonation reaction is conducted at very low temperatures (such as $-20°$ C.), the kinetic energy of the high speed mixing or agitating environment aids in the sulfonation reaction.

Sulfonation reactions that take place in a high speed mixing or agitating environment typically prevent the polymer from settling and/or precipitating out of the solvent. As one of skill in the art would recognize, the speed that is needed to prevent the molecule from precipitating out of the solvent may vary depending on the particular equipment (such as a spinning plate thin film reactor, or a counter-rotating shaft thin film reactor) used for the sulfonation reaction. Thus, the high-speed mixer assists in maintaining the reaction components in solution or dynamic mixture and prevents the sulfonated polymer from aggregating.

The sulfonation reaction process may further be varied by the sequence in which the reactants are added to the reaction mixture or solution. In certain embodiments, the sulfonation reaction components may be added in any order or simultaneously. In other embodiments, the polymer is dissolved in or otherwise placed in contact with one or more non-reactive solvent(s) prior to contact with sulfur trioxide and/or the optional electron pair donor agent(s). In other particular embodiments, the non-reactive solvent may be first placed in contact with sulfur trioxide and/or the optional electron pair donor agent(s) prior to adding the polymer. In still other particular embodiments, the polymer may be placed in contact with sulfur trioxide and/or the optional electron pair donor agent(s) prior to addition of the non-reacting solvent. Thus, in certain embodiments, the sulfur trioxide utilized in the processes disclosed herein is present in the reaction in the form of free sulfur trioxide. In certain other embodiments, the sulfur trioxide utilized in the processes disclosed herein is present in the reaction in the form of a coordination complex with at least one electron pair donor agent. In some particular embodiments, the non-reacting solvent is capable of forming a coordination complex with the sulfur trioxide.

Depending on several factors, including the starting polymer and the degree of sulfonation desired, as well as the overall sulfonation reaction kinetics, the sulfonation reaction can be completed within the range of approximately 5 to 2,000 seconds (or approximately 33 minutes). In certain embodiments, the reaction kinetics allow for the reaction to be completed within approximately 1 second, 2 seconds, 3 seconds, 4 seconds, 5 seconds, 10 seconds, 20 seconds, 30 seconds, 40 seconds, 50 seconds, 60 seconds, 70 seconds, 80 seconds, 90 seconds, 100 seconds, 120 seconds, 140 seconds, 160 seconds, 180 seconds, 200 seconds, 300 seconds, 400 seconds, 500 seconds, 600 seconds, 800 seconds, 1000 seconds, 1500 seconds, 2000 seconds, or any value there between. In certain embodiments, the sulfonation reaction takes no more than approximately 6 hours, 5 hours, 4 hours, 3 hours, 2 hours, 1 hour, or a half-hour. In certain embodiments, the reaction is complete within approximately two minutes or less, one minute or less, or 30 seconds or less, or any value there between.

The sulfonation reaction can be terminated by exhausting reaction components, or quenching by the addition of water or other sacrificial reactant (such as ethanol or methanol or amines such as ammonia). Alcohols convert sulfur trioxide to esters of sulfuric acid, thus ceasing sulfonation of the polymer. However, it is worth noting that such (sulfonic acid) esters are potent alkylating agents and must be handled with care. In addition, it is possible to terminate the reaction by selecting and adding a solvent capable of separating the sulfonated polymer from the reaction system, i.e. precipitation.

Once the sulfonation reaction has been terminated, the sulfonated polymer may then be isolated by filtration, precipitation, chromatography, or other purification methods known in the art. The sulfonated polymer may be washed (if necessary), by standard techniques known in the art. For example, the sulfonated polymer may be washed by submersion in a washing liquid (including but not limited to deionized water or an aqueous salt solution) followed by filtration, or spray washed on a film evaporator. The use of an aqueous salt solution as a means of generating the polymeric salt may be preferable, if the sulfonated polymer is not required to be in acid form although it is necessary to rinse excess salt solution from the polymer prior to its use in further processes.

Another method involves the preparation of a blend by combining the sulfonated polymer solution, immediately post sulfonation, with a solution of another polymer (or polymers) to comprise the blend, mixing the two solutions adequately and isolating the blend by precipitation or solvent removal by means standard in the industry (such as reduced pressure rotary evaporation or spray drying). An ensuing purification step to remove any traces of sulfuric acid (for example) alleviates the need to first isolate and purify the sulfonated polymer, redissolve and combine with another polymer to form the blend. The aforementioned and described manipulation removes an entire step as described in the latter example. The polymer may then be dried at room temperature or at elevated temperature and under vacuum (negative or reduced pressure). In other embodiments, the blended polymeric solution may be cast, sprayed, or isolated as a solid and subsequently subjected to thermoforming (simultaneous cospraying of solutions of sulfonated and non-sulfonated polymers, lamination of non-sulfonated polymer film with either sulfonated polymer film or films comprised of blends of sulfonated and non-sulfonated polymer film or lamination of blend films with sulfonated polymer film.

As disclosed herein inter alia, another beneficial feature of the disclosed process includes the cost-saving ability to recycle the sulfonation reaction solvent(s) and optional electron pair donor agent(s). As described herein, the electron pair donor agent does not chemically participate in the sulfonation reaction. Thus, it can be easily removed from the sulfonated polymer at the termination of the sulfonation reaction. In the case of dioxane, residual traces evaporate from the precipitated sulfonated polymer during the drying step. The ability to reuse or recycle the solvent(s) and/or electron pair donor agent(s) of the presently disclosed process makes the processes disclosed herein amenable to use a multitude of polymers in a wide variety of applications.

In addition to batch processing, the presently disclosed methods of sulfonating polymers may be utilized for large scale sulfonation of polymers by utilizing a continuous feed process, i.e. an industrial scale apparatus that moves the polymer to be sulfonated continuously through a sulfonating reaction mixer and into a holding tank once sulfonated. In this regard, the throughput of the process is increased by several orders of magnitude. Such a large-scale process increases yield, lowers cost, and produces more uniform sulfonated polymers, all of which make it readily adaptable for commercialization.

Sulfonated Polymers

Previously used processes for sulfonating polymers, such as polymers, with sulfur trioxide resulted in high levels of cross-linking polymers and high levels of undesirable side-products. (U.S. Pat. Nos. 2,475,886; 2,283,236; and 2,533,211, all of which are hereby incorporated by reference in their entirety).

The sulfonated polymers generated by the herein disclosed processes include sulfonated and/or polysulfonated oligomers and/or polymers and/or copolymers containing, for example, either alkene and/or arene and/or hydroxyl moieties with little or no residual or contaminating sulfuric acid remaining following removal of water from the solvent(s). In certain embodiments, the sulfonation reaction is performed under an anhydrous and controlled atmosphere, which may include inert gases such as argon, nitrogen or the like. Depending on the particular starting material, the resulting sulfonated polymers (such as a sulfonated ionomeric copolymer) may be soluble in water, or insoluble in water but soluble in alcohol (for example n-propanol or butyl alcohol or any variety of binary, ternary or higher solvent mixtures).

Additionally, the sulfonated polymers generated by the processes disclosed herein will have little, if any, cross-linking polymeric components or other undesirable side-products. In embodiments that utilize an ionomeric copolymer in the sulfonation reaction there will be little or no resulting cross-linked ionomeric copolymer(s).

Furthermore, the sulfonated polymers generated by the disclosed process are very uniformly sulfonated or polysulfonated. In certain embodiments, the sulfonated polymer is uniformly sulfonated or polysulfonated from approximately 20%, 30%, 40%, 50%, 60%, 70%, 80%, 85%, 90%, 91%, 92%, 93%, 94%, 95%, 96%, 97%, 98%, 99% by weight, or greater or any value there between. In certain embodiments, the sulfonated polymer prepared by the disclosed process is uniformly sulfonated or polysulfonated at 10-90% by weight.

Uniformly sulfonated polymer membranes (such as sulfonated polymer membranes) typically have higher ionic conductivities, higher water transfer rates, and reduced water absorption at lower sulfonation mole percent conversion levels than non-uniformly sulfonated polymer of the same chemical structure. Thus, one of skill in the art would infer uniformity of a particular sulfonated polymer based on several polymer mechanical and electrochemical properties, as demonstrated for the uniformly sulfonated polymers disclosed herein.

The method of sulfonating arene-containing polymers and the various sulfonated polymers disclosed herein may be used directly or further modified before use. For example, the sulfonated polymers disclosed herein may be used as the free acid or as a salt thereof such as that of an alkali metal, or other metal salt thereof, including but not limited to metal ions, preferably mono-, di- and trivalent ions of metals in Groups IA, IB, IIA, IIB, IIIA, IIIB, and VIII of the Periodic Table of Elements. The metal ions may be complexed or uncomplexed, and can be used alone or in any mixture thereof. Some examples of suitable metal ions include: lithium, sodium, potassium, rubidium, silver, mercury, copper, magnesium, calcium, strontium, cadmium, tin, iron, barium, palladium, scandium, yttrium, and cesium salts, or any combination thereof. Compounds of these metals may be used as hydroxides, chlorides, bromides, fluorides, oxides, alcoholates, hydrides, carboxylates, formates, acetates, alkoxides such as methoxides or ethoxides, nitrates, carbonates, bicarbonates, and the like.

The degree of neutralization with a metal ion-containing base may be achieved by various methods known in the art. In particular, the neutralization reaction may be carried out by adding the metal compound, directly or in solution, to a solution of the sulfonated polymer and, following neutralization, precipitating and separating the resulting polymer. Another particular method of neutralization may entail melt blending the sulfonated polymer with the metal compound. This reaction is preferably conducted at elevated temperatures in order to facilitate homogenous distribution of the metal compound and to volatize any neutralization byproduct that can include water, alcohols, and small organic species.

Alternatively, the sulfonated polymer may already be in an all neutralized salt form or in a partially neutralized form and protonation (acidification) is desired. Acidification of the sulfonated polymer may be carried out under conditions, which allow for a homogenous uniform distribution of the acid in the sulfonated polymer. The resulting metal-salt acidification product may then be used directly or treated further in order to remove any metal salt by-product.

The degree of sulfonation and/or neutralization may be measured by several techniques that are readily available to the skilled artisan. For example, nuclear magnetic resonance (NMR), titration, or elemental analysis may be used to determine the overall degree of functionality. Moreover, the sulfonated polymers may be analyzed for sulfonation and other characteristics by using Fourier Transform Infrared spectroscopy (FTIR) or other technique in conjunction with optical spectroscopy, infrared spectroscopy, nuclear magnetic resonance, electron spin resonance and others. In addition, the titration of a solution of a block copolymer with a strong base may be utilized to determine the degree of functionality and/ or neutralization (metal sulfonate salt content). Neutralization is generally based on the percentage of sulfonate ions as compared to the total sulfonic acid and sulfonate group functionality. Purity may be assessed by a number of methods that include liquid chromatography, in particular gel permeation chromatography (GPC) and mass spectrometry (matrix assisted laser desorption ionization—MALDI MS) as well as indirectly by a variety of in vitro and in vivo biocompatibility tests that include but are not limited to in vitro cytotoxicity by MEM or direct contact methods as well as by implantation of the material and subsequent histopathology of the excised tissue from around the implanted material.

Moreover, compositions and articles prepared by the sulfonated polymers disclosed herein may also contain non-reactive additives, such as chemical additives, fillers, or reinforcements, which do not react with the sulfonated polymer. Some examples include, but are not limited to plasticizers, lubricants, anti-oxidants, anti-static agents, colorants, flame retardants, fillers, mold release agents, nucleating agents, stabilizers or inhibitors of oxidative, thermal and ultraviolet light degradation, and fibrous or other reinforcements (including but not limited to silica, carbon black, clay, glass fibers, organic fibers, calcium carbonate, and the like).

The sulfonated polymers disclosed herein may be further modified before use by processes, such as cross-linking, that improve their mechanical properties. In other embodiments the polymer to be sulfonated may be preformed or cross-linked, or a combination of the two prior to sulfonation. For example, a cross-linked bead of styrene-divinyl benzene copolymer may be subjected to sulfonation to yield an ion-exchange bead or may be insoluble in the sulfonation solvent medium thus resulting in sulfonation of the surface. For example polyethylene terephthalate or parylene may be sulfonated by the sulfonating complex without the aggressive and degradative affects of neat sulfur trioxide.

In certain embodiments disclosed herein, the sulfonated polymer have a total mole percent (mol %) sulfonation of approximately 2-99% or greater. In specific embodiments, the mol % of sulfonation is approximately 2%, 5%, 10%, 20%, 25%, 30%, 40%, 50%, 60%, 70%, 75%, 80%, 90%, 91%, 92%, 93%, 94%, 95%, 96%, 97%, 98%, 99%, 99.5%, or greater or any value there between. The mole % of sulfonation may be varied during the process to produce from 5-99% sulfonation. The sulfonated polymers disclosed herein exhibit exceptionally good qualities. Depending on the particular starting material, qualities such as toughness, clarity, formability, oil/grease resistant barrier, draw ability, heat seal, hot tack, abrasion resistance, electrical conductivity, tensile strength, stiffness, hardness, tensile impact, stress crack resistance, adhesion, durability, and melt strength are enhanced by the sulfonation process disclosed. The sulfonated polymers may be used for sizing agents, protective colloids, adhesives, dispersing agents, thickening agents, tanning agents, packaging resins, conventional extrusion/co-extrusion blown film, cast film, other films, extrusion coating equipment, molding resins, automotive parts, golf ball resins, packaging seals, molded goods (e.g. cosmetics, or sporting goods), and may be used for electro spraying or electro spinning in the form of a fiber, foam, sheet, or encapsulate, or any combination thereof.

In certain embodiments, membranes may be produced utilizing the sulfonated polymers disclosed herein by spray processing, such as thermal spray coating. Thermal spray processing allows for a relatively thin (approximately 0.005") and thick (approximately 0.250") coatings of polymers onto a variety of materials and is effective to produce protective barriers. Some examples of polymers that have been used for thermal spraying include but are not limited to polyethylene, poly(methylmethacrylate), poly(ethylene-methylmethacrylate) copolymer, ethylene methacrylic acid copolymer, polyetheretherketone polymer, polyphenylene sulfide liquid crystal polymer, polyamide (nylon), phenolic epoxy, Tefzel, and post consumer comingled polymer.

In general, the polymer powder is injected into a heat source (such as a flame or plasma) and moved to a pre-heated substrate by way of a spray gun or other apparatus. The thickness of the coating depends on the number of passes of the spray gun across the substrate.

In still other embodiments, membranes may be produced utilizing the sulfonated polymers disclosed herein by melt extrusion. Generally, melt extrusion involves feeding polymers into a drive extruder as raw plastic material, which transports the material to a die head while it is simultaneously heated, mixed, pressurized and metered. At the die head, the polymer takes up the approximate shape of the article and is then cooled either by water or air to give the final shape. As the polymer cools it is drawn along by haul-off devices and either coiled (for soft products) or cut to length (for hard products).

In addition to the above-mentioned processes, membranes may also be produced using sulfonated polymers disclosed herein by using a rotogravure process or a slot casting process. For a slot casting process, the polymer dissolved in a solvent is pressure extruded in a uniform thickness and viscosity onto carrier or support creating a continuous film. Rotogravure is a process wherein a cylinder with surface cavities is coated with a liquid. As the cylinder turns, it transfers the liquid in the surface cavities to a carrier or support forming a continuous film. Generally, uniformly sulfonated polymer casts evenly with little or no signs of macro-phase separation. When membrane casting is even, it produces stronger membranes because the density and cross-sectional thickness are uniform.

The polymeric blend materials may further be electrospun or electrosprayed directly from solution to form tubes, rods, and other formed materials. In certain aspects, the polymeric blend materials may be spun into fibers for vascular grafts or other applications.

Certain embodiments relate to a polymer blend that is insoluble in water and is composed of a sulfonated aryl-containing copolymer and at least one material selected from the group consisting of homo-polymer or copolymers. The homo-polymer or copolymers may comprise polyurethane, a segmented polyurethane, an arylene-vinyl containing block copolymer, a polysiloxane, a polyamide, a polyurethane urea, a polyketone, a polyester, a poly(ether-ester) (such as polydioxanone), a polyanhydride, a poly(ortho ester), a polyacrylate, a polyalkylene, a polycarbonate, a poly(carbonate urethane) a fluoropolymer, a polysulfone, carbohydrate polymers (such as cellulose and starch), a polypeptide, a polyether, and/or a poly(vinylalcohol), poly(ethylene-co-vinyl acetate), poly(ethylene-co-vinyl alcohol). In certain embodiments, the sulfonated copolymer comprises a block copolymer with at least two polymer end blocks (A) and at least one polymer interior block (B) wherein: a. each (A) block is a polymer block resistant to sulfonation and each (B) block is a polymer block susceptible to sulfonation, said (A) and (B) blocks containing no significant levels of olefinic unsaturation; b. each (A) block independently having a number average molecular weight between 1,000 and 60,000 and each (B) block independently having a number average molecular weight between 2,000 and 300,000; c. each (A) block comprising one or more segments selected from poly-merized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof, wherein any segments containing polymerized 1,3-cyclodiene or polymerized conjugated dienes are subsequently hydrogenated and wherein any (A) block comprising polymerized ethylene or hydrogenated polymers of a conjugated, acyclic diene have a melting point greater than 50° C.; d. each (B) block comprising segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof; e. said (B) blocks are sulfonated to the extent of 10 to 100 mol percent, based on the units of vinyl aromatic monomer in said (B) blocks; and f. the mol percent of vinyl aromatic monomers which are unsubstituted styrene monomers, ortho-substituted styrene monomers, meta-substituted styrene monomers, alpha-methylstyrene, 1,1-diphenylethylene and 1,2-diphenylethylene in each (B) block being between 10 mol percent and 100 mol percent.

In other embodiments, the sulfonated copolymer comprises a triblock copolymer in which the end blocks (B) are comprised of arylene-vinyl polymer segments and the central block (A) is comprised of a diene polymer segment comprising repeat units of at least four carbon atoms. In certain instances, the (B) blocks are susceptible to sulfonation and the (A) blocks are resistant to sulfonation. In some cases, the aryl-containing sulfonated copolymer is an arylene-vinyl containing copolymer prepared by anionic polymerization, or cationic polymerization.

In certain embodiments, the sulfonated arylene-vinyl containing copolymer comprises a hydrogenated central block. In some cases, the sulfonated arylene-vinyl containing copolymer is prepared by cationic polymerization and comprises a saturated central block. In some embodiments, the sulfonated block copolymer is a triblock copolymer (A-B-A) in which the end blocks are comprised of arylene-vinyl polymer and the central block is comprised of a monoalkene polymer comprising repeat units of at least four carbon atoms. In other embodiments, the sulfonated copolymer is a pseudo-random block copolymer in which the end blocks are comprised of arylene-vinyl polymer and the central block is comprised of a diene polymer comprising repeat units of at least four carbon atoms. In particular embodiments, the sulfonated copolymer is a random block copolymer in which the end blocks are comprised of arylene-vinyl polymer and the central block is comprised of a diene polymer comprising repeat units of at least four carbon atoms.

In certain embodiments, the sulfonated copolymer is a random copolymer comprising an arylene-vinyl monomer and a non-arylene-vinyl comonomer. In other embodiments, the sulfonated copolymer is an aryl-containing condensation polymer. The condensation copolymer may comprise a polyurethane, a polyamide, a polyester, a polysiloxane, or a polycarbonate.

In some embodiments, the sulfonated copolymer may have the general configuration A-D-B-D-A, A-B-D-B-A, $(A-D-B)_nX$, $(A-B-D)_nX$, or mixtures thereof, where n is an integer from 2 to about 30, and X is coupling agent residue wherein: a. each A block and each D block is a polymer block resistant to sulfonation and each B block is a polymer block susceptible to sulfonation, said A, B and D blocks containing no significant levels of olefinic unsaturation; b. each A block independently having a number average molecular weight between 1,000 and 60,000 and each B block independently having a number average molecular weight between 2,000 and 300,000; c. each A block comprising one or more segments selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof, wherein any segments containing polymerized 1,3-cyclodiene or conjugated dienes are subsequently hydrogenated; d. each B block comprising segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof; e. each D block comprises polymers having a glass transition temperature less than 20° C. and a number average molecular weight of between 1,000 and 50,000, said D block being selected from the group consisting of (i) a polymerized or copolymerized conjugated diene selected from isoprene, 1,3-butadiene having a vinyl content prior to hydrogenation of between 20 and 80 mol percent, (ii) a polymerized acrylate monomer, (iii) a silicon polymer, (iv) polymerized isobutylene and (v) mixtures thereof, wherein any segments containing polymerized 1,3-butadiene or isoprene are subsequently hydrogenated; f said B blocks are sulfonated to the extent of 10 to 100 mol percent, based on the units of vinyl aromatic monomer in said B blocks; and g. the mol percent of vinyl aromatic monomers which are unsubstituted styrene monomers, ortho-substituted styrene monomers, meta-substituted styrene monomers, alpha-methylstyrene, 1,1-diphenylethylene and 1,2-diphenylethylene in each B block being between 10 mol percent and 100 mol percent.

In other embodiments, the sulfonated block copolymer comprises at least one A block comprising polymers of one or more para-substituted styrene monomers selected from para-methylstyrene, para-ethylstyrene, para-n-propylstyrene, para-iso-propylstyrene, para-n-butylstyrene, para-sec-butylstyrene, para-iso-butylstyrene, para-t-butylstyrene, isomers of para-decylstyrene, and isomers of para-dodecylstyrene. The sulfonated block copolymer A block may be a polymer block of para-t-butylstyrene and said B block is a polymer block of unsubstituted styrene. Alternatively, the A block is a polymer block of para-methylstyrene and said B block is a polymer block of unsubstituted styrene.

In some embodiments, the sulfonated block copolymer contains a D block prior to hydrogenation wherein the D block is a polymer block of 1,3-butadiene, and wherein 20 to 80 mol percent of the condensed butadiene units in block D have 1,2-configuration prior to hydrogenation. In particular instances, the sulfonated block copolymer may be formed into articles that are insoluble in water and have the general configurations A-B-A, A-B-A-B-A, $(A-B-A)_nX$, $(A-B)_nX$ or mixtures thereof, where n is an integer from 2 to about 30, and X is coupling agent residue and each A block is a polymer block resistant to sulfonation and each B block is a polymer block susceptible to sulfonation, said A and B blocks containing no significant levels of olefinic unsaturation, wherein: a. each A block comprising one or more segments selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof, wherein any segments containing polymerized 1,3-cyclodiene or polymerized conjugated dienes are subsequently hydrogenated and wherein any A block comprising polymerized ethylene or hydrogenated polymers of a conjugated, acyclic diene have a melting point greater than 50° C.; b. each B block is a copolymer block of at least one conjugated diene and at least one mono alkenyl arene selected from (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof, wherein said B block is subsequently hydrogenated; c. each A block having a number average molecular weight between 1,000 and 60,000 and each B block having a number average molecular weight between 10,000 and 300,000; d. the weight percent of mono alkenyl arene in each B block being between 5 percent and 100 percent; e. the total amount of mono alkenyl arene in the sulfonated block copolymer being 20 percent weight to 80 percent weight; and f. said B blocks are sulfonated to the extent of 10 to 100 mol percent, based on the units of vinyl aromatic monomer in said B blocks.

In some embodiments, the sulfonated copolymer comprises a polyethersulfone, a polyetherketone, a methylmethacrylate, a triblock, such as a styrene-isobutylene-styrene, or an A block comprising polymers of one or more para-substituted styrene monomers selected from para-methylstyrene, para-ethylstyrene, para-n-propylstyrene, para-isopropylstyrene, para-n-butylstyrene, para-sec-butylstyrene, para-iso-butylstyrene, para-t-butylstyrene, isomers of para-decylstyrene, and isomers of para-dodecylstyrene.

In some embodiments, the sulfonated triblock copolymer contains a B block comprising polymers of one or more alkylene monomers selected from variations of isobutylene, methyl cyclohexene, methylcyclopentene, 1-methyl, 1'-ethyl ethane (and higher alkyl derivatives). In some embodiments, the copolymer comprises polyester (polylactides, polyglycolides, lactide-glycolide copolymers, terephthalate, and the like).

The sulfonated polymers and the blends disclosed herein may be used in a variety of industrial settings and for a variety of applications. One of skill in the art could adapt or modify the sulfonated polymers and the subsequent blends described herein in order to be included in a variety of applications. Further embodiments of the present invention include processes for manufacturing various articles or compositions by utilizing the sulfonated polymers and/or blends described herein.

One of skill in the art would fully appreciate that the various articles may be further processed or have any number of other components present, including other sulfonated polymers or unsulfonated polymers. For example, certain articles may comprise a therapeutic or other agent including but not limited to antimicrobial agents (such as antibacterial, antifungal, antiviral—including inhibiting Human Immunodeficiency Virus and Herpes Simplex Virus, spermicide, antiparasitic or other agent), anesthetics, growth factors, anti-inflammatory agents, antihistamines, analgesics, antineoplastic agents, hormones, tranquilizers, metals, vitamins, minerals, amino acids, nucleic acids, cytokines, and the like). In certain embodiments, such as for use of the sulfonated polymers as membranes, it may be necessary that any such additive be miscible with the sulfonated polymer, not compromise the mechanical strength or integrity of the membrane, and/or not reduce the moisture transfer of the membrane.

Thus, for certain embodiments, the sulfonated polymers and/or blends may be molded, dipped, fiber spun, extruded or otherwise processed into articles. The articles may take the form of a film, sheet, coating, band, strip, profile, molding, foam, tape, fabric, thread, filament, ribbon, bead (including microbeads and nanobeads), other spheres (including microspheres and nanospheres), knit, weave, fiber, plurality of fibers, fibrous web, or any combination thereof. Any of these forms may be solid, perforated, laminated, woven, non-woven, porous, non-porous, or the like and any combination thereof. In addition, the sulfonated polymers and/or blends may be utilized in various durable or consumable goods.

For example, the sulfonated polymers and/or blends disclosed may be used in various forms in the textile industry (such as for spinning fibers, fabrics, or polymeric blends); or in leather tanning (for example, for coating leather articles). The sulfonated polymers and/or blends may be combined with any natural or synthetic fabric, including but not limited to polyester fabric, poly(ethylene terephthalate) fabric, rayon fabric, acrylic fabric, polymeric fabric, cotton, jute, silk, wool, linen, twill, toile, bunting, duck, faille, gabardine, herringbone, jacquard, muslin, lawn, leno, paper or plant based fabrics, or others. Some examples of articles that may be manufactured from the sulfonated polymers and their blends include clothing (including but not limited to shirts, jackets, pants, shoes, boots, socks, hats, bodysuits, gloves, head coverings, hazardous material protective clothing, gas and liquid filters, tarps & drapes, including surgical drapes, goggles, etc.), blankets, rugs, furniture, carpeting, other floor coverings, and the like.

Additionally, the sulfonated polymer and/or blend materials can be used where one or more properties are desired, such as good material compatibility, good wet adhesion, good wet strength, adjustable water absorption, good water and proton transport characteristics, good biocompatibility, facile processing (such as easy film or membrane formation), adjustable drug-matrix properties, adjustable barrier properties, adjustable flexibility and elasticity, adjustable hardness, and adjustable biological activity.

Specifically, in certain embodiments, the sulfonated polymer and/or blended materials may be adapted for use in surgery or other articles related to medical intervention for diagnosis, treatment, or prevention of disease or a biological disorder. For example, tissue engineering; artificial neuron fibers; medical or dental cement; drug delivery formulations; pharmaceutical compositions; implantable medical devices such as stents, catheters, cannulae, tubing (such as dialysis tubing), drug delivery patches, surgical repair patches, shunts, vascular grafts, artificial organ surfaces (such as heart, kidney, liver, pancreas, or other organ), heart valves, pacemakers, kidney dialysis, implants, artificial joints, intrauterine devices, microspherical particles for embolic therapy and/or drug delivery, contact lenses, assist device surfaces, including prostheses, or various other implantable devices or surfaces, wound dressings (such as gauze dressings, bandages, sutures, and the like).

In certain embodiments, the sulfonated polymer and/or blended materials disclosed herein may be adapted to for use as equipment coatings; coatings for medical devices (such as biosensors, electrodes including iontophoretic drug delivery patches, stent grafts, heart assists, etc.), adhesives, fluid absorbing materials, water gels, including bodily-fluid absorbing materials (such as internal or external pads, tampons or other material for use as for wounds, disposable diapers, urinary incontinence products, feminine hygiene products, lactation or nursing products, and the like); IV bags, blood bags, medical articles, such as hospital gowns, laboratory wipe, surgical drapes, bedding, protective scrubs or clothing; coatings on tables; countertops; floors; or laboratory equipment, etc.

In certain embodiments, the absorbent articles comprising the sulfonated polymer and or blended materials described herein may be neutralized with ammonia in order to provide protection against bacterial growth and related odor. Such super absorbent materials may be mixed in a fibrous matrix, such as wood pulp. Super absorbent particles and materials comprising the sulfonated polymer and/or blended materials described herein would generally have an absorbent capacity of at least about 6 grams of liquid per gram of fluff, or at least about 10 grams of liquid absorbance, or at least about 20 grams of liquid absorbance, or at least about 40 grams of liquid absorbance. In some embodiments, the sulfonated copolymer may be left in its acid form so as to absorb putrid amino compounds (that are liberated in the breakdown of amino acids and proteins) and may be useful where ammonia production is high.

In certain embodiments, the blends incorporating sulfonated polymers disclosed herein may be utilized as matrices for oral pharmaceutical formulations, suppositories, vaginal inserts, condoms, and other medical devices.

Due to the improved properties of the membranes resulting from blends incorporating sulfonated polymers, such as the ability to be processed and formed without degradation, the membranes may also be utilized as air filters, medical clothing (such as in human and veterinary medical facilities), where protective clothing and breathable fabrics are necessary. Further, the membranes, coated fabrics, fabric laminates, and fabrics created from spun fibers could provide a barrier of protection from various environmental elements (wind, rain, snow, chemical or biological organisms and agents) while offering a level of comfort as a result of their ability to rapidly transfer water from one side of the membrane or fabric to the other. Thus, in certain instances moisture from perspiration can escape from the surface of the skin and full enclosure suits fashioned from the membranes and fabrics can provide protection to responders at emergency situations where smoke, chemical spills, or various chemical or biological agents are a possibility.

The polymer blends incorporating sulfonated polymers disclosed herein may further be used in various applications in occupational safety or homeland security, including polymer electrolyte membranes (PEMs) for chemical or biological protection clothing, instruments or other articles; fluid treatment (for example, membranes for fluid or gas treatment including desalination or other filtration of water, filtration of blood or other bodily fluids, filtration of food or beverages, filtration of indoor or outdoor air, etc.), and the like.

Certain other embodiments relate to utilizing the sulfonated polymer membrane blends described herein for use with environmental control elements (such as for heating, ventilating, air conditioning, cooling, humidity control, air filtration, etc.), and may include membranes, sensors, gauges, unitary humidity exchange cell (HUX), and the like.

The homogeneity of the sulfonated polymers disclosed herein make these products and processes particularly suitable for producing membranes for applications that require a high degree of uniform properties. Furthermore, the disclosed processes yield sulfonated polymers with a lower level of conversion to get the useful sulfonated polymer. Thus, in one example, the sulfonated polymers may be used to form ion conducting membranes, such as when cast from high dielectric constant solvents and are insoluble in water.

The sulfonated copolymers used for certain blends and resulting membranes disclosed herein are preferably water-insoluble (having a solubility of less than 0.5 grams of polymer in 100 grams of water at 100° C.).

In other embodiments, the polymeric blends described herein may be used as marine or other coatings to prevent fouling in a moist environment, such as high humidity or aqueous immersion. The hydrophilic and anionic nature of the sulfonated polymeric blend materials would serve to prevent attachment of any variety of microorganisms, including bacteria, algae, plants, mollusks, and others.

Sulfonated copolymers, as used in polymer electrolyte membranes, generally exhibit good electrical conductivity (J. Electrochem. Soc., 142: L21-L23 (1995)), low methanol crossover rate (J. Electrochem. Soc., 143: 1233-1239 (1996)); excellent thermal stability (J. Electrochem. Soc. 143: 1225-1232 (1996)); very low or nearly zero water drag coefficient (J. Electrochem. Soc. 143: 1260-1263 (1996)); as well as enhanced activity for oxygen reduction (J. Electrochem. Soc. 144: 2973-2982 (1997)). Accordingly, certain sulfonated polymers disclosed herein may be useful as polymer electrolyte membranes.

In certain other embodiments, the sulfonated copoloymers and their blends disclosed herein may be adapted for use in the electronics field, such as for electrochemical devices (including membranes for fuel cells or fuel devices, and batteries); in testing assays or sensors (including biosensors, microfluidic devices, cell impedance sensors, moisture and/or heat transfer membranes, semiconductor chips or other computer parts, ultra-capacitors, other capacitors, other electronic sensors, or the like). Certain such embodiments are taught in U.S. Pat. Nos. 5,679,482; 5,468,574, 6,110,616, 6,413,298; and 6,383,391, which is hereby incorporated by reference in its entirety.

A fuel cell device generates electricity directly from a fuel source, such as hydrogen gas, and an oxidant, such as oxygen or air. A fuel cell typically comprises of two catalytic electrodes separated by an ion-conducting membrane. The fuel gas (e.g. hydrogen) is ionized on one electrode, and the hydrogen ions diffuse across the membrane to recombine with the oxygen ions on the surface of the other electrode. If current is not allowed to run from one electrode to the other, a potential gradient is built up to stop the diffusion of the hydrogen ions. Allowing some current to flow from one electrode to the other through an external load produces power.

In certain embodiments, the membrane made from the sulfonated molecules disclosed herein, is mechanically stable, allows the diffusion of ions from one electrode to the other while preventing the flow of electrons, and/or keeps the fuel and oxidant gases apart. Diffusion or leakage of the fuel or oxidant gases across the membrane leads to explosions or other undesirable consequences.

Certain other embodiments relate to utilizing the sulfonated molecules described herein for use with environmental control elements (such as for heating, ventilating, air conditioning, cooling, humidity control, etc.), and may include membranes, sensors, gauges, unitary humidity exchange cell (HUX), and the like.

The homogeneity of the sulfonated molecules disclosed herein make these products and processes particularly suitable for producing membranes for applications that require a high degree of uniformity of properties. Furthermore, the disclosed processes yield sulfonated molecules with a lower level of conversion to get the useful sulfonated molecule. Thus, in one example, the sulfonated molecules may be used to form ion conducting membranes, such as when cast from high dielectric constant solvents and are insoluble in water.

The sulfonated copolymers used for certain membranes, including those blended systems, disclosed herein are preferably water-insoluble (having a solubility of less than 0.5 grams of polymer in 100 grams of water at 100° C.).

For example, HUX cells may comprise a membrane that is utilized for transferring water or other polar liquids or gases (including vapors) from one side of the cell to the other side of the cell by action of a difference in some quantity or gradient across the cell. This transfer of water or gas may or may not be accompanied by evaporation of the water or gas into or from the stream by the absorption of heat or diabatic means. The membrane gradient may be produced by vapor pressure, osmotic or hydrostatic pressure, chemical, thermochemical, electrochemical, magnetochemical potential difference, or thermal, electric, electromagnetic, thermoelectric, or electrothermal potential difference. Examples of applications of HUX include but are not limited to pervaporation, humidification and dehumidification of fuel cell streams in stacks and devices, drying gases at pressure, tertiary oil recovery, process control for synthetic manufacture of chemicals for which water is a reactant, isolation of minerals from mining fluids, industrial separation of oil-water emulsions, microfiltration and ultrafiltration of colloidal suspensions and biological or organic macromolecules for purification, maintaining water content of methanol in direct methanol fuel cells, reverse osmosis for isolation of fresh water from brine, electrolysis cells, dialysis, electro-dialysis, piezo-dialysis, electro-osmosis and chloro-alkali cells.

Still other embodiments relate to adapting the sulfonated macromolecule or their blends disclosed herein for use as immersion coatings (such as for marine paints and coatings); other coatings (such as for drag reduction for cars, boats, aircraft, motorcycles or other motorized vehicles); consumable products (such as consumer electronics, appliances, toys, furniture, or packing materials); food and beverage industry (for example for cartons, containers, packaging, jars, boxes, food wrapping, or the like); outdoor articles (such as tents, soil coverings, tarps, recreational equipment, boating gear, lifevests, and the like); building materials or other composites, as well as other applications.

EXAMPLES

The following examples are meant to be representative only, and not limiting in any way.

Example 1

Blending SSIBS with TPU

Sulfonated Styrene-Isobutylene-Styrene (SSIBS) polymer solutions (9 to 15% solid) were prepared. SSIBS product varied in sulfonation levels from 30 to 65 mol %.

Thermoplastic Polyurethane (TPU) (medical grade, Noveon) solutions were prepared (9% solid) by dissolving the TPU in tetrahydrofuran (THF) and were utilized to blend with the SSIBS solutions. The TPUs utilized were:
1. TECOPHILIC hydrophilic aliphatic polyether-based TPU (high moisture absorption).
2. TECOFLEX aliphatic polyether-based TPU.
3. CARBOTHANE aliphatic polycarbonate-based polyurethane.
4. TECOPLAST aromatic polyether-based TPU.

BIONATE polycarbonate urethane from the Polymer Technology Group, Inc. was also prepared (6.7% solid) by dissolving in DMAC(N,N-dimethylacetamide).

The following polymer blends were produced utilizing the above constituents:
A. Blend 56 mol % SSIBS/TECOPHILIC hydrophilic aliphatic polyether-based TPU in 50/50 by weight: TECOPHILIC hydrophilic aliphatic polyether-based TPU/THF solution (11 g, 9% solids) was added to the SSIBS polymer solution (10 g, 10% solids, 56 mol % sulfonation) by way of pipette while stirring, and continuous stirring overnight at 40° C. A clear solution resulted and a clear, transparent membrane was obtained following casting.
B. Blend 56 mol % SSIBS/TECOFLEX aliphatic polyether-based TPU in 50/50 by weight: TECOFLEX aliphatic polyether-based TPU/THF solution (11 g, 9% solids) was added to the SSIBS polymer solution (10 g, 10% solids, 56 mol % sulfonation) by way of pipette while stirring and continual stirring overnight at 40° C. A clear solution resulted and a clear, transparent membrane was obtained following casting.
C. Blend 56 mol % SSIBS/CARBOTHANE aliphatic polycarbonate-based polyurethane in 50/50 by weight: CARBOTHANE aliphatic polycarbonate-based polyurethane/THF solution (11 g, 9% solids) was added to the SSIBS polymer solution (10 g, 10% solids, 56 mol % sulfonation) by way of pipette while stirring and continual stirring overnight at 40° C. A homogenous solution was obtained and a clear, transparent membrane was obtained following casting.
D. Blend 52 mol % SSIBS/TECOPLAST aromatic polyether-based TPU in 50/50 by weight: TECOPLAST aromatic polyether-based TPU/THF solution (11 g, 9% solids) was added to the SSIBS polymer solution (8 g, 12.6% solids, 52 mol % sulfonation) by way of pipette while stirring and continual stirring overnight at 40° C. A homogenous solution was obtained and a clear, transparent membrane was obtained following casting.
E. Blend 52 mol % SSIBS/TECOPHILIC hydrophilic aliphatic polyether-based TPU in 75/25 by weight: TECOPHILIC hydrophilic aliphatic polyether-based TPU/THF solution (22 g, 9% solids) was added to the SSIBS polymer solution (40 g, 15% solids, 52 mol % sulfonation) by way of pipette while stirring, and continual stirring overnight at 40° C. A clear solution resulted and a clear, transparent membrane was obtained following casting.
F. Blend 52 mol % SSIBS/TECOFLEX aliphatic polyether-based TPU in 75/25 by weight: TECOFLEX aliphatic polyether-based TPU/THF solution (11 g, 9% solids) was added to the SSIBS polymer solution (20 g, 15% solids, 52 mol % sulfonation) by way of pipette while stirring and continual stirring overnight at 40° C. A clear solution resulted and a clear, transparent membrane was obtained following casting.
G. Blend 52 mol % SSIBS/CARBOTHANE aliphatic polycarbonate-based polyurethane in 75/25 by weight: CARBOTHANE aliphatic polycarbonate-based polyurethane/THF solution (11 g, 9% solids) was added to the SSIBS polymer solution (23.8 g, 12.6% solids, 52 mol % sulfonation) by way of pipette while stirring and continual stirring overnight at 40° C. A homogenous solution resulted and a clear, transparent membrane was obtained following casting.
H. Blend 40 mol % SSIBS/TECOPHILIC hydrophilic aliphatic polyether-based TPU in 50/50 by weight: TECOPHILIC hydrophilic aliphatic polyether-based TPU/THF solution (11 g, 9% solids) was added to the SSIBS polymer solution (8.7 g, 11.5% solids, 40 mol % sulfonation) by way of pipette while stirring and continual stirring overnight at 40° C. A homogenous solution resulted and a clear, transparent membrane was obtained following casting.
I. Blend 40 mol % SSIBS/TECOFLEX aliphatic polyether-based TPU in 50/50 by weight: TECOFLEX aliphatic polyether-based TPU/THF solution (11 g, 9% solids) was added to the SSIBS polymer solution (8.7 g, 11.5% solids, 40 mol % sulfonation) by way of pipette while stirring and continual stirring overnight at 40° C. A homogenous solution resulted and a clear, transparent membrane was obtained following casting.

J. Blend 50 mol % SSIBS/BIONATE polycarbonate urethane in 50/50 by weight: BIONATE polycarbonate urethane/DMAC solution (54 g, 6.7% solids) was added to the SSIBS polymer solution (24 g, 15% solids, 50 mol % sulfonation) by way of pipette while stirring and continual stirring overnight at 40° C. A homogenous solution resulted and a clear, transparent membrane was obtained following casting.

Example 2

Blending SSIBS with Silicon Urethane Copolymers

SSIBS polymer solutions (9 to 15% solids) were prepared with varying sulfonation levels (30-65 mol %). Two silicone urethane copolymers (available under the trade designations PURSIL and CARBOSIL from the Polymer Technology Group, Inc. were utilized in the experiments. PURSIL silicone urethane copolymer is a silicone polyether urethane and CARBOSIL silicone urethane copolymer is a silicone polycarbonate urethane.

The silicone urethane copolymer/DMAC solutions (7 to 9%) were prepared by dissolving the polymer resin in DMAC. The following blends were prepared: (Note: THF can be used as well as the solvent)

a. Blend: 50 mol % SSIBS/PURSIL silicone urethane copolymer 50/50 by weight: PURSIL silicone urethane copolymer/DMAC solution (44 g, 9% solids) was added to the SSIBS polymer solution (31.7 g, 12.6. % solids, 50 mol % sulfonation) by way of pipette while stirring and continual stirring overnight at 40° C. A homogenous solution resulted and a clear, transparent membrane was obtained following casting.

b. Blend: 50 mol % SSIBS/CARBOSIL silicone urethane copolymer 50/50 by weight: CARBOSIL silicone urethane copolymer/DMAC solution (57 g, 7% solids) was added to the SSIBS polymer solution (27 g, 15% solids, 50 mol % sulfonation) by way of pipette while stirring and continual stirring overnight at 40° C. A homogenous solution resulted and a clear, transparent membrane was obtained following casting.

c. Blend: 50 mol % SSIBS/PURSIL silicone urethane copolymer 75/25 by weight: PURSIL silicone urethane copolymer/DMAC solution (22 g, 9% solids) was added to the SSIBS polymer solution (57 g, 10.5% solids, 51 mol % sulfonation) by way of pipette while stirring and continual stirring overnight at 40° C. A homogenous solution resulted and a clear, transparent membrane was obtained following casting.

d. Blend: 50 mol % SSIBS/CARBOSIL silicone urethane copolymer 75/25 by weight: CARBOSIL silicone urethane copolymer/DMAC solution (28.6 g, 7% solids) was added to the SSIBS polymer solution (57 g, 10.5% solids, 51 mol % sulfonation) by way of pipette while stirring and continual stirring overnight at 40° C. A homogenous solution resulted and a clear, transparent membrane was obtained following casting.

Example 3

Cast Membrane of Blend SSIBS with TPUs and SSIBS with Silicone Urethane Copolymers The above polymer blended solutions were slot cast onto silicone-coated polyester release liners on heated vacuum assisted casting tables with different blade settings. Membranes of different thickness resulted. The membranes were dried to remove solvent in a lab fume hood.

The prepared membranes were evaluated using a routine moisture transfer test based on DI water uptake at room temperature for 3 and 24 hours as well as total mass (moisture & ion) uptake in 0.9% saline solution at 50° C. for 3 and 24 hours. The results of these tests are detailed in Table 1.

TABLE 1

SSIBS-Polyurethane total water absorbance data (0.9% saline, 50° C.)

| Formulation | % mass uptake @ 3 hours |
|---|---|
| 56 mol % SO$_3$H SSIBS | 187 |
| 56 mol % SO$_3$H SSIBS:TECOPHILIC hydrophilic aliphatic polyether-based TPU (50:50) | 153 |
| 56 mol % SO$_3$H SSIBS:TECOFLEX aliphatic polyether-based TPU (50:50) | 174 |
| 56 mol % SO$_3$H SSIBS:CARBOTHANE aliphatic polycarbonate-based polyurethane (50:50) | 123 |
| 56 mol % SO$_3$H SSIBS:TECOPLAST aromatic polyether-based TPU (OP) (50:50) | 110 |
| 56 mol % SO$_3$H SSIBS:TECOPLAST aromatic polyether-based TPU (TP) (50:50) | 97.7 |
| 56 mol % SSIBS:PURESIL silicone urethane copolymer (50:50) | 54 |
| 56 mol % SSIBS:CARBOSIL silicone urethane copolymer (50:50) | 62 |

Example 4

Laminate Preparations from Blended Membranes

Two types of laminated samples were prepared. The first type of sample was assembled by preparing a sandwich of two layers (4×4 inch, or approximately 10.16 cm×10.16 cm) of TEGAPORE material (3M, Minneapolis, Minn.) with the blended membrane (4×4 inch, or approximately 10.16 cm×10.16 cm). This tri-layer membrane sandwich was then laminated at a temperature range of approximately 80-120° C.

The second type of sample was assembled by cutting TEGAPORE material into two exact sizes of frame shape with an overhanging edge of approximately 0.5 inches (1.27 cm) and assembling the blended membrane with the two frame shaped TEGAPORE material and then laminating them together at a temperature range of approximately 80-120° C.

Example 5

Conversion of the Laminated Samples into the Sodium Form

The laminated membrane samples were immersed in sodium bicarbonate (aqueous solution of approximately 3%) at room temperature for 15 minutes. The membranes were then removed from the solution, excess solution was removed by shaking the membranes, and the membranes were set on paper towels to dry, thereby producing the sodium form of the laminated membrane samples.

The sodium form of the laminated membrane samples were then treated with doxycycline by immersing the sodium form of the laminated membrane samples in doxycycline (aqueous solution, 1 g of doxycycline in 1 L deionized water) at room temperature for 15 minutes. The membranes were then removed from the doxycycline solution, excess solution was removed by shaking the membranes, and the membranes were set on paper towels to dry. The release of doxycycline tracks water absorbance with the SSIBS:SIBS blend showing release out beyond 72 hours. The results of this water absorbance are shown in Table 2. As can be seen, the wet mechanical properties of the sulfonated polymer membranes increased, and adhesion to stainless steel and glass improved as the SIBS component increased.

TABLE 2

SSIBS-SIBS water absorbance data

| Formulation | 2 h | 3 h | 24 h | 48 h | 72 h |
|---|---|---|---|---|---|
| 56 Mol % SSIBS:SIBS (50/50) | 26% | 33% | 34% | 40% | 43% |
| 56 Mol % SSIBS:SIBS (60/40) | 13% | 26% | 31% | 39% | 44% |
| 56 Mol % SSIBS:SIBS 75/25 | 114% | 116% | 124% | 131% | 135% |
| 56 Mol % SSIBS:SIBS 90/10 | 153% | 187% | 199% | 203% | 206% |

Example 6

Modified Sulfonated Styrene Block Copolymers for Vascular Applications

We have prepared sulfonated polymeric blends as described herein to produce blended materials of sulfonated SIBS (block copolymers) combined with polyurethane (such as polycarbonate urethane, polysiloxy urethane, and polyether urethane) as well as sulfonated SIBS. The membrane films were prepared by solvent casting onto siliconized release liner, or a PTFE sheet. We have characterized the saline water absorbance characteristics of these materials as well as their ability to release (retain) a water soluble drug (Doxycycline) that binds to the sulfonate group of the polymer, and the ability of these blended materials to deter the attachment of platelets under static conditions.

In platelet adhesion studies, 16 mm diameter discs of SSIBS (56 mol %) were cut from solvent cast films of 50:50 SSIBS:SIBS using a cork-borer and the cut films were placed in well plates, washed and incubated with PBS (phosphate buffered solution) overnight. Next, the discs were exposed to human platelet rich plasma for one hour, washed with PBS, and stained with FITC-anti-CD41a. Finally, the discs were fixed with 4% paraformaldehyde and imaged using an epifluorescent microscope at 40×. PTFE control samples were prepared in the same fashion, exposed to platelet rich plasma, fixed, and imaged in parallel.

Figure 2:
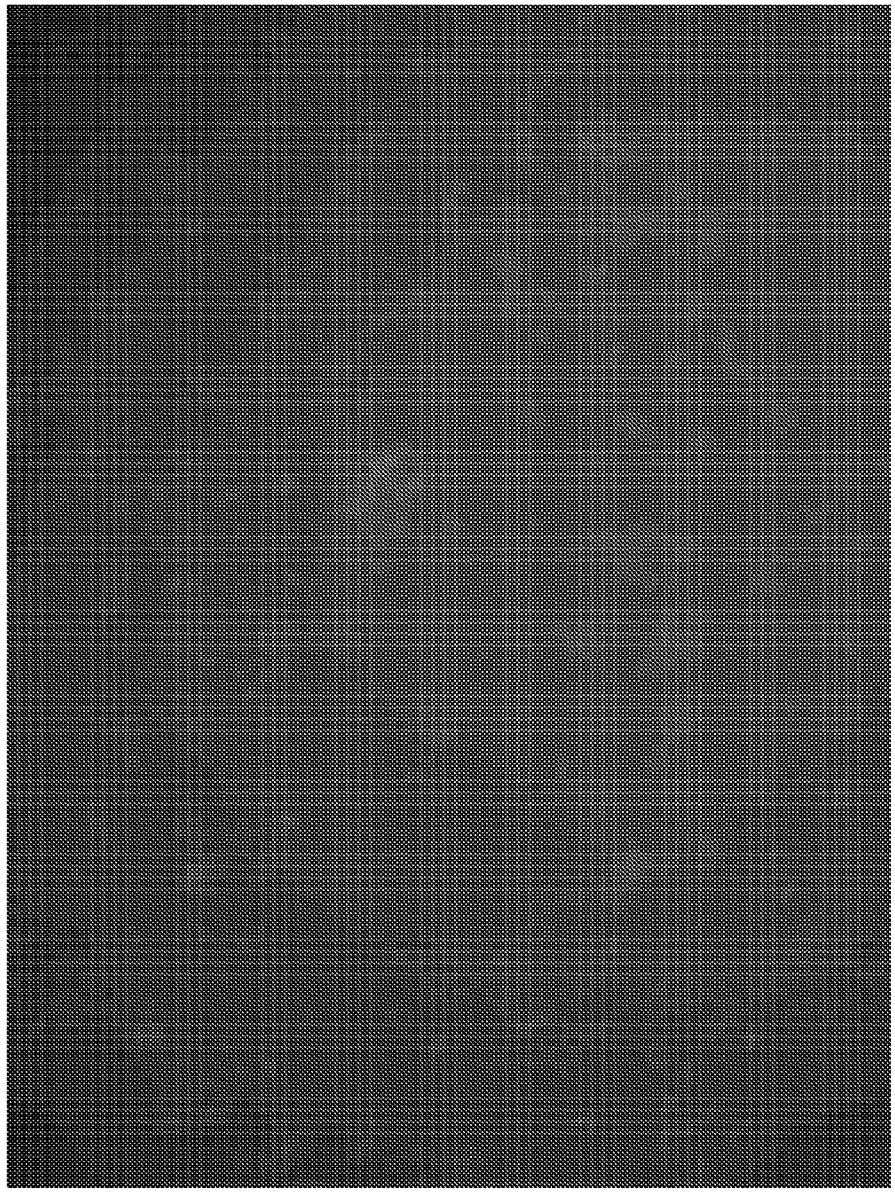
FIG. 2 shows platelet aggregation for CARBOSIL silicone urethane copolymer/SSIBS polymeric blended materials.
Figure 3:
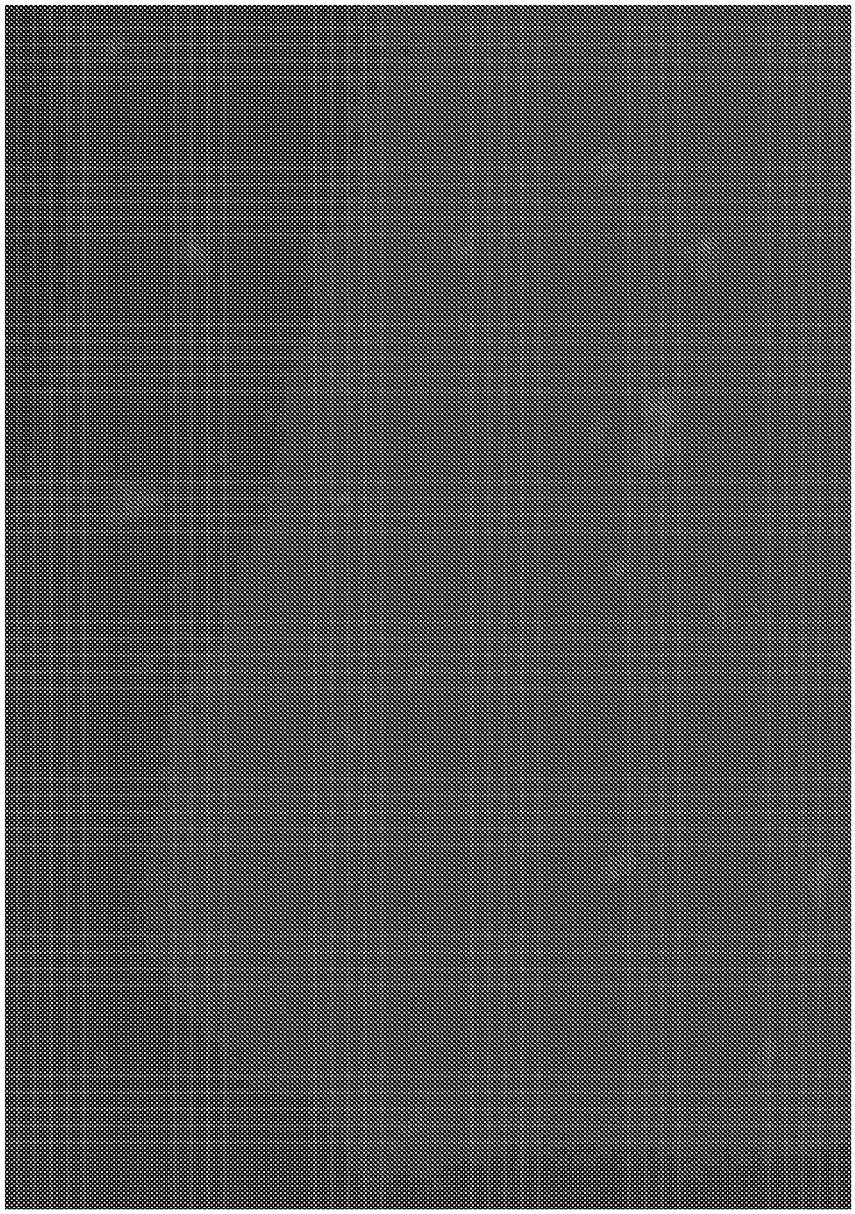
FIG. 3 shows platelet aggregation for SB3T-024/SIBS (50:50) sodium salt form polymeric blended materials.
Figure 4:
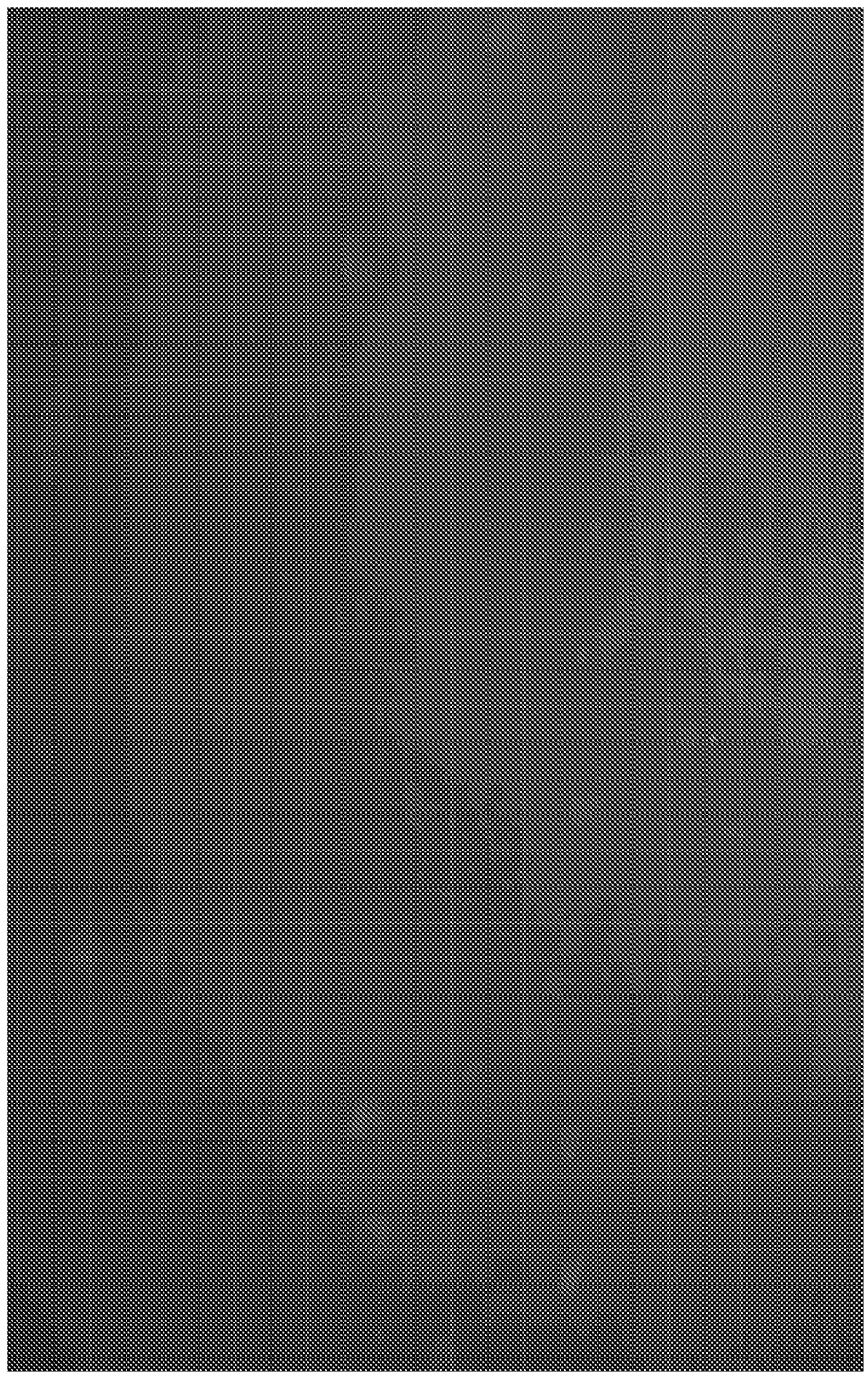
FIG. 4 shows platelet aggregation for SB3T-024/SIBS (50:50) acid form for polymeric blended materials.

SSIBS (56 mol % sulfonation) blended with the non-sulfonated SIBS polymer in a ratio of 50:50 w/w with SSIBS in its acid form and in its sodium salt form as prepared by exposure to 0.9% normal saline (ion exchange) showed very high levels of resistance to platelet adhesion and very little platelet aggregation relative to the control PTFE sample, and were comparable to negative controls such as albumin coated surfaces. Further, the platelets that attached to these surfaces did not appear to be activated to any significant degree as evidenced by a lack of spreading pseudopods. Results are shown in FIGS. 2-4.

Doxycycline release from the same 50:50 blend of SSIBS:SIBS/Na+ form (following incorporation by 10 minute exposure to 0.1M aqueous Doxycycline:HCl) was produced from a thin film over a 72 hour period in 37° C. PBS. At 72 hours the doxycycline is still present in the sample, but is approaching equilibrium (FIG. 1). Thus, the membranes described herein can bind cations and retain cations for extended time periods that will allow for use with endothelial cell attachment. Other membranes tested included SB3T-30/56-024/SIBS (60:40)-Na+, CARBOSIL silicone urethane copolymer/SSEBS (50:50), and SBT-30/40-013 Teco (50:50). Furthermore, co-spraying a SSIBS lacquer simultaneously with a SIBS-peptide laquer is believed to yield improved incorporation into the material.

Studies conducted with the same polymer blends and PE-anti-CD 62P (anti-P selectin) (Invitrogen) staining provided similar results with regard to anti-thrombotic characteristics of the polymer blend materials tested.

Example 7

Capillary Rheometry Results

The thermal processing characteristics, such as shear viscosity rates, of several exemplary sulfonated polymer blend membranes were tested by capillary rheometry. Generally, sulfonated polymers, particularly in their acid forms, are not stable to temperatures necessary to thermally process into sheet, film, rod, tube, or complex form by way of transfer molding, injection molding, press molding, extrusion or the like. This is because desulfonation (and subsequent liberation of $SO_3$) leads to decomposition and charring. In addition, block polymers in some cases are not amenable to extrusion or transfer molding due to the high melt viscosities of these materials.

Briefly, each blend sample was test extruded through a die of defined dimension, and the shear pressure drop across the die was recorded at a set volumetric flow rate. The pressure drop was measured as each sample being tested was extruded through the die.

Figure 5:
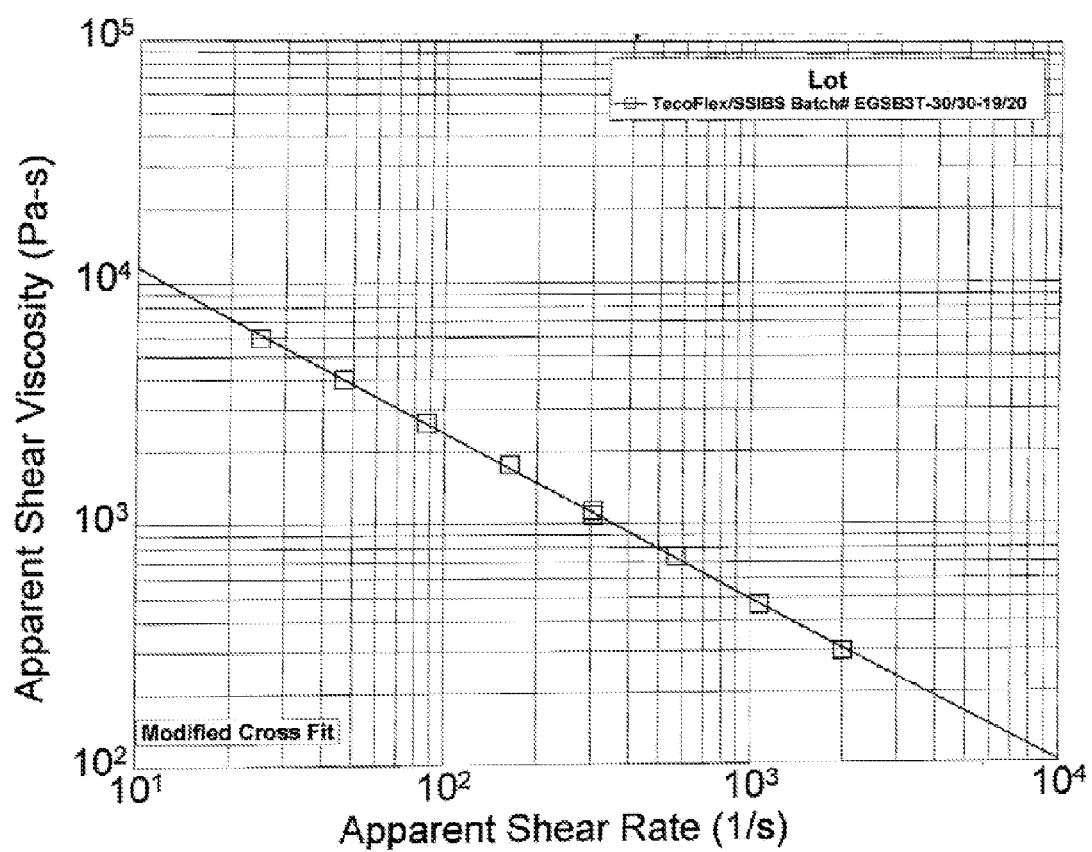
FIG. 5 shows capillary rheometry results presented as a graph depicting the shear sweep of TECOFLEX aliphatic polyether-based TPU EG80A/SSIBS Blend (70:30), as described in working Example 7 herein.
Figure 6:
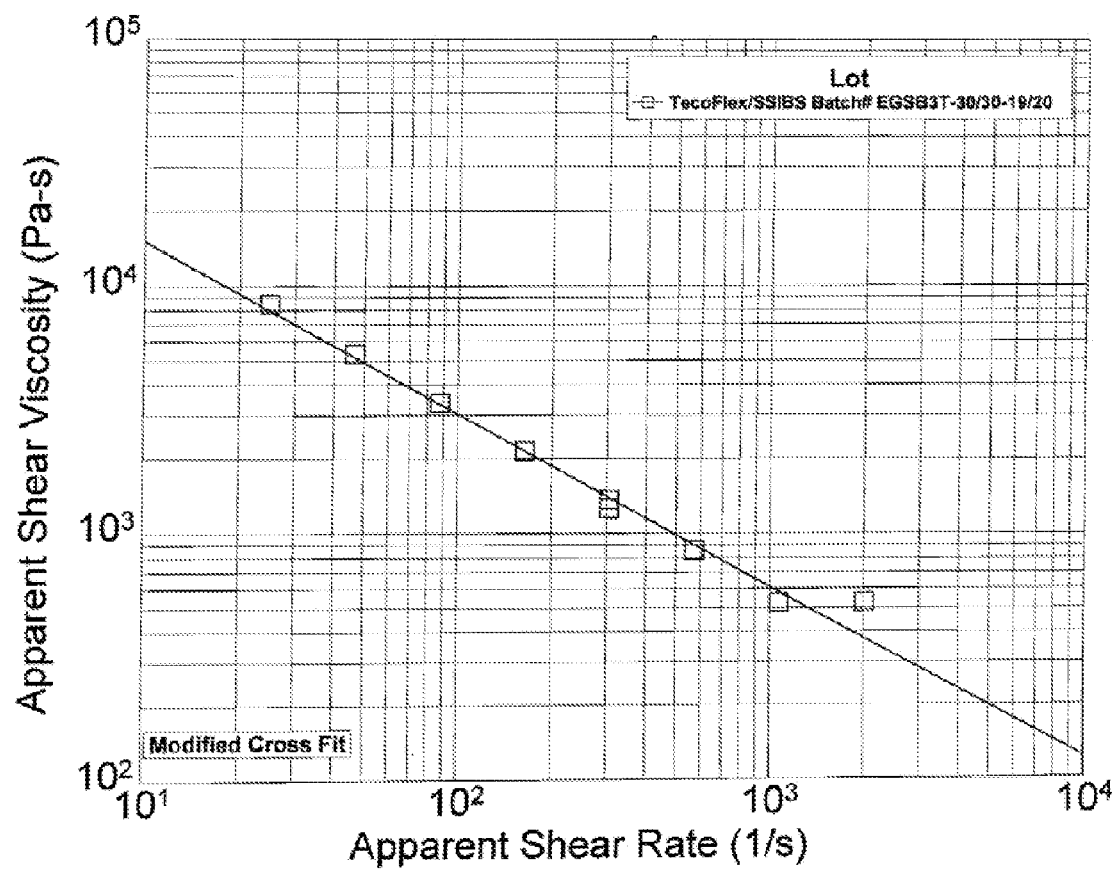
FIG. 6 shows capillary rheometry results presented as a graph depicting the shear sweep of TECOFLEX aliphatic polyether-based TPU EG80A/SSIBS Blend (50:50), as described in working Example 7 herein.

In this particular Example, a Dynisco LCR 7001 Capillary Rheometer was utilized with a die dimension of 20 mm length by 1 mm diameter (180° entrance angle). Predrying was accomplished using a vacuum oven at 70° C. for 4 hours. Sensor 1 force values indicate the load cell readings in Newtons (N), where values less than 100N are below the sensitivity of the load cell. Results are shown in Tables 3 and 4, and also represented in FIGS. 5 and 6, respectively,

TABLE 3

TECOFLEX aliphatic polyether-based TPU EG80A/SSIBS Blend (70:30), Temperature of 177° C., Shear Rates of 2000 to 25 $sec^{-1}$, melt time of 360 seconds

| Point | Sensor Force (N) | Position (mm) | RamRate (mm/min) | Time (min) | Shear Stress (kPa) | Shear Rate (1/s) | Shear Viscosity (Pa-s) |
|---|---|---|---|---|---|---|---|
| 1 | 3429 | 132.8 | 164.8 | 6.20 | 598.33 | 2004.55 | 298.49 |
| 2 | 2864 | 152.3 | 88.1 | 6.42 | 499.79 | 1071.90 | 466.27 |
| 3 | 2422 | 157.2 | 47.1 | 6.52 | 422.56 | 573.16 | 737.25 |
| 4 | 1988 | 162.3 | 25.2 | 6.73 | 348.65 | 306.46 | 1137.66 |
| 5 | 1660 | 169 | 13.5 | 7.23 | 289.63 | 163.93 | 1766.77 |
| 6 | 1327 | 172.7 | 7.2 | 7.74 | 231.58 | 87.68 | 2641.09 |
| 7 | 1076 | 175.6 | 3.9 | 8.50 | 187.77 | 46.82 | 4010.37 |
| 8 | 858 | 177.3 | 2.1 | 9.32 | 149.64 | 25.05 | 5973.00 |
| 9 | 1910 | 183.2 | 25.2 | 9.55 | 333.34 | 306.46 | 1087.68 |

TABLE 4

TECOFLEX aliphatic polyether-based TPU
EG80A/SSIBS Blend (50:50), Temperature of 177° C.,
Shear Rate of 2000 to 25 sec$^{-1}$, melt time of 360 seconds

| Point | Sensor Force (N) | Position (mm) | RamRate (mm/min) | Time (min) | Shear Stress (kPa) | Shear Rate (1/s) | Shear Viscosity (Pa-s) |
|---|---|---|---|---|---|---|---|
| 1* | 6055 | 127.5 | 164.8 | 6.17 | 1056.55 | 2004.55 | 527.08 |
| 2 | 3238 | 189.5 | 88.1 | 6.87 | 565.07 | 1071.90 | 527.17 |
| 3 | 2815 | 193.8 | 47.1 | 6.97 | 491.16 | 573.16 | 856.92 |
| 4 | 2406 | 197.1 | 25.2 | 7.10 | 419.81 | 306.46 | 1369.86 |
| 5 | 2017 | 201.6 | 13.5 | 7.43 | 352.00 | 163.93 | 2147.23 |
| 6 | 1697 | 203.8 | 7.2 | 7.73 | 296.19 | 87.68 | 3378.00 |
| 7 | 1431 | 205.8 | 3.9 | 8.25 | 249.70 | 46.82 | 5333.12 |
| 8 | 1218 | 207.1 | 2.1 | 8.87 | 212.53 | 25.05 | 8483.49 |
| 9 | 2218 | 220 | 25.2 | 9.39 | 387.03 | 306.46 | 1262.90 |

*Point 1 is not valid due to the elasticity of the material. The material was forced down in the barrel but air was still present through the beginning of the run. These data indicate two important points: (1) The materials that were tested both melted and extruded from the barrel with the demonstrated formation of a continuous rod of the blend material, and (2) the extruded material did not reveal any discoloration indicating that the sulfonated material has not undergone any sulfonation.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims

The invention claimed is:

1. A polymeric material that is water insoluble and comprises (i) at least one uniformly sulfonated aryl-containing block copolymer comprising at least one arene moiety-containing unit and at least one non-arene moiety containing unit, wherein said sulfonated aryl-containing block copolymer is 50-80 mol % sulfonated; wherein said sulfonated aryl-containing block copolymer comprises a random block copolymer, a triblock copolymer, or a pseudorandom block copolymer wherein the end blocks comprise arylene-vinyl polymer and the central blocks comprise at least one monoalkene polymer segment prepared from a monoalkene selected from the group consisting of isobutylene, methyl cyclohexene, and methylcyclopentene, and (ii) at least one thermoplastic or thermosetting non-sulfonated homopolymer or copolymer selected from the group consisting of polyurethane, a segmented polyurethane, a poly(ether urethane), a poly(carbonate urethane), a poly(siloxy urethane), a polyurethane urea, an arylene-vinyl containing block copolymer, a polysiloxane, a polyamide, a polyketone, a polyester, a poly(ether-ester), a polyanhydride, a polyamine, a poly(ortho ester), a polyacrylate, a polyalkylene, a polycarbonate, a fluoropolymer, a polysulfone, carbohydrate polymers, a polypeptide, a polyphosphazine, a polyether, a poly(ether sulfone), a poly(vinylalcohol), poly(ethylene-co-vinyl acetate), poly(ethylene-co-vinyl alcohol), a poly(epoxide)-polyamine curing system, and an acrylate.

2. The polymeric material of claim 1, wherein said uniformly sulfonated aryl-containing block copolymer comprises a pseudo-random block copolymer or a random block copolymer wherein the end blocks comprise arylene-vinyl polymer.

3. The polymeric material of claim 1, wherein said uniformly sulfonated aryl-containing block copolymer comprises polyethersulfone, polyetherketone, polystyrene, methylmethacrylate, polydioxanone, polylactides, polyglycolides, lactide-glycolide copolymers or polyesters.

4. An article of manufacture made with the polymeric material of claim 1, wherein said article is selected from the group consisting of a membrane, a medical device, a pharmaceutical composition, a moisture transfer membrane, a fluid-absorbing material, a fuel cell, a capacitor, a wound dressing, a fabric, a building material, a desalination membrane or device, a membrane for heating, a membrane or device for ventilating and air conditioning (HVAC), a packing material, a surface coating, a shunt, a stent, tubing, clothing, bedding, surface coatings, fluid absorbing materials, adhesives, fluid collection or storage bags, sensors, gauges, and fluid filters.

5. A method of making the polymeric material of claim 1, wherein said method comprises the steps of combining at least one of said uniformly sulfonated aryl-containing block copolymer in solution with at least one of said thermoplastic or thermosetting non-sulfonated homopolymer or copolymer, allowing the solution to thoroughly mix, and isolating and/or processing the polymer blend.

6. The method of claim 5 wherein said step of isolating and/or processing the polymer blend comprises at least one of spray drying, precipitation, solvent evaporation, extruding, electrospraying, electrospinning, and precipitating the polymer blend.

7. The method of claim 5 further comprising the step of converting the polymer blend to salt form.

8. A method of making an article of manufacture comprising the polymeric material of claim 1, comprising the steps of combining at least one of said uniformly sulfonated aryl-containing block copolymer in solution with at least one of said thermoplastic or thermosetting non-sulfonated homopolymer or copolymer, allowing the solution to thoroughly mix, isolating the polymer blend, and manipulating the polymer blend to form the article.

9. The method of claim 8, wherein said step of manipulating the polymer blend comprises at least one of thermal lamination, transfer molding, press molding, extruding, thermal fiber-spinning, electrospinning, electrospraying, painting, dipping, and pressure spraying.

* * * * *

UNITED STATES PATENT AND TRADEMARK OFFICE
CERTIFICATE OF CORRECTION

PATENT NO.       : 8,586,637 B2
APPLICATION NO.  : 12/664762
DATED            : November 19, 2013
INVENTOR(S)      : Vachon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 677 days.

Signed and Sealed this
Twenty-second Day of September, 2015

Michelle K. Lee
*Director of the United States Patent and Trademark Office*